(12) United States Patent
Ono et al.

(10) Patent No.: US 8,383,829 B2
(45) Date of Patent: *Feb. 26, 2013

(54) ELECTROCHROMIC COMPOUND, ELECTRODE, AND DISPLAY ELEMENT

(75) Inventors: Kaori Ono, Tokyo (JP); Osamu Ishige, Kanagawa (JP); Takeshi Hakii, Kanagawa (JP); Akihito Hisamitsu, Kanagawa (JP)

(73) Assignee: Konica Minolta Holdings, Inc., Tokyo (JP)

( * ) Notice: Subject to any disclaimer, the term of this patent is extended or adjusted under 35 U.S.C. 154(b) by 817 days.

This patent is subject to a terminal disclaimer.

(21) Appl. No.: 12/419,319

(22) Filed: Apr. 7, 2009

(65) Prior Publication Data

US 2009/0256121 A1    Oct. 15, 2009

(30) Foreign Application Priority Data

Apr. 15, 2008   (JP) .................................. 2008-105504

(51) Int. Cl.
*C07F 7/18*   (2006.01)
*C07F 7/10*   (2006.01)

(52) U.S. Cl. .................. 548/110; 548/335.1; 548/335.5; 548/336.1; 548/342.5; 548/343.5; 252/600

(58) Field of Classification Search .................. 548/110, 548/335.1, 335.5, 336.1, 342.5, 343.5; 252/600
See application file for complete search history.

(56) References Cited

U.S. PATENT DOCUMENTS

| | | | | |
|---|---|---|---|---|
| 8,049,948 B2 * | 11/2011 | Hakii et al. | .................... | 359/265 |
| 2007/0197604 A1 * | 8/2007 | Beavers et al. | ................ | 514/340 |
| 2009/0027757 A1 * | 1/2009 | Kokeguchi et al. | ............ | 359/273 |
| 2011/0013261 A1 * | 1/2011 | Hattori et al. | ................. | 359/297 |

FOREIGN PATENT DOCUMENTS

| | | | |
|---|---|---|---|
| JP | 2007031708 A | * | 2/2007 |
| WO | WO 2006129424 A1 | * | 12/2006 |

OTHER PUBLICATIONS

Zhao et al. "Organic and inorganic hybrid film with second-order nonlinear optical and pyroelectric properties" Thin Film Solids 2006, 515, 1748-1752.*
Machine translation of JP 2007031708 A.*
Full English Translation of JP2007031708A.*

* cited by examiner

*Primary Examiner* — Mark Kaucher
(74) *Attorney, Agent, or Firm* — Lucas & Mercanti, LLP

(57) ABSTRACT

An electrochromic compound represented by Formula (1),

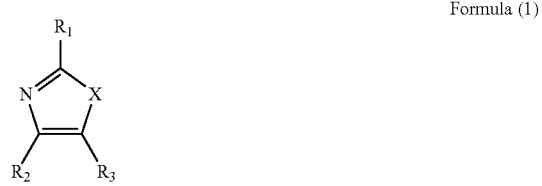

Formula (1)

wherein $R_1$ is an alkyl group, an alkenyl group, an aryl group, or a heterocyclic group; $R_2$ and $R_3$ are each a hydrogen atom or a substituent; X is N—$R_4$, an oxygen atom, or a sulfur atom; and $R_4$ is a hydrogen atom or a substituent; provided that at least one of $R_1$-$R_4$ has a partial structure represented by Formula (2),

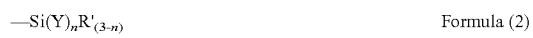

Formula (2)

wherein Y is a halogen atom or OR, R is an alkyl group, or an aryl group; R' is an alkyl group, an alkenyl group, an aryl group, or a heterocyclic group, and n is an integer of 1-3.

1 Claim, 3 Drawing Sheets

ELECTROCHROMIC COMPOUND, ELECTRODE, AND DISPLAY ELEMENT

This application is based on Japanese Patent Application No. 2008-105504 filed on Apr. 15, 2008, in Japanese Patent Office, the entire content of which is hereby incorporated by reference.

TECHNICAL FIELD

The present invention relates to a new electrochromic compound, an electrode, and a display device.

BACKGROUND

In recent years, along with the enhancement of operation speed of personal computers, the spread of network infrastructure, and an increase in capacity and a decrease in price of data storage, the opportunities of obtaining pieces of information such as documents and images, which have been provided as prints on paper, as simpler and easier electronic information, and browsing them have been increasing.

As media displaying such electronic information, recently, an electronic paper has been widely developed as an electronic medium being closer to paper in place of existing displays such as a CRT or a liquid crystal display. For example, an electrochromic display element utilizing coloring and discoloring properties of electrochromic compounds has been widely studied and developed from material development to device designing, since the electrochromic display element is a reflection type display element, exhibits memory characteristics, and can be driven at low voltage. In addition, since the electrochromic display element can develop various colors depending on a structure of the materials, it is also expected to be useful for a multicolor display element.

In recent years, as materials for realizing an electronic device such as those typified by electronic paper, organic-inorganic composite materials have been actively researched. For example, an electrochromic compound has been used, in which the compound is adsorbed on a nano-crystalline layer deposited on an electrode (refer, for example, to Patent Documents 1 and 2).

However, most of the examples have been the developments, as described above, such that a terminal of an acid group of functional organic materials such as a phosphoric acid, a carboxylic acid, and a salicylic acid is adsorbed to hydroxyl groups of inorganic fine particles. Thus, an organic compound can be adsorbed on the inorganic fine particles by employing such acid groups described above, but its bonding force is not so strong that the bonds between the organic compound and the inorganic fine particles are easily broken during fabrication of devices or after repeatedly using the device, or under alkaline conditions to result in problems.

Conventionally, the surface treatment of inorganic fine particles using an organic compound has been widely performed. An example being applied to an electronic device has been disclosed, in which a metal oxide is treated with a silane coupling agent to improve its surface properties (refer, for example, to Patent Document 3), but, the above example simply aimed to improve surface properties of inorganic fine particles. Further, another example of organic-inorganic composite materials was disclosed, in which a metal oxide was treated with a silane coupling agent, and then allowed to react with a functional organic material to produce a bonding between them through a silanol bond (refer, for example, to Patent Document 4). However, the above example had problems such as exhibiting no memory characteristics, low efficiency of the reaction between the functional organic material and the metal oxide so that the control of the amount of the reaction being difficult, and low production adaptability due to complicated production steps of an electrode.

The inventors carried out a diligent examination, and as a result, the inventors found that the above problems can be resolved by introducing a functional silane (a hydrolysable group such as an alkoxysilane or halosilane) as a substituent into an electrochromic compound exhibiting a specific structure.

Patent Document 1: Japanese Translation of PCT International Application Publication No. 2000-506629
Patent Document 2: Unexamined Japanese Patent Application Publication No. (hereinafter, referred to as JP-A) 2007-304164
Patent Document 3: JP-A 2004-191418
Patent Document 4: JP-A 2007-31708

SUMMARY

Disclosure of the Invention

Problems to be Solved by the Present Invention

The present invention has been achieved in consideration of such problems. An object of the present invention is to provide electrochromic compounds exhibiting excellent memory characteristics and coloring stability over time, and electrodes and display elements, being excellent in production adaptability, and employing the above compounds.

Means to Solve the Problems

The above issues of the present invention can be solved by the constitutions below.

Item 1. An electrochromic compound represented by Formula (1) below,

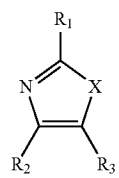

Formula (1)

In Formula (1), $R_1$ is an alkyl group, an alkenyl group, an aryl group, or a heterocyclic group; $R_2$ and $R_3$ are each a hydrogen atom or a substituent; X is N—$R_4$, an oxygen atom, or a sulfur atom; and $R_4$ is a hydrogen atom or a substituent; provided, however, that at least one of $R_1$ to $R_4$ has a partial structure represented by Formula (2).

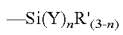

$$—Si(Y)_n R'_{(3-n)}$$ 
Formula (2)

In Formula (2), Y is a halogen atom or OR, in which R is an alkyl group, or an aryl group. R' is an alkyl group, an alkenyl group, an aryl group, or a heterocyclic group. And n is an integer of 1-3.

Item 2. The electrochromic compound described in above Item 1, wherein Y is OR in above Formula (2).

Item 3. The electrochromic compound described in above Item 1 or 2, wherein R' is an alkyl group in above Formula (2).

Item 4. The electrochromic compound described in any one of above Items 1-3, wherein X is N—$R_4$ in above Formula (1).

Item 5. An electrode on which an electrochromic compound described in any one of above Items 1-4 is chemically bonded.

Item 6. The electrode described in above Item 5, wherein the above-described electrode is a transparent electrode.

Item 7. A display element employing the electrode described in Item 5 or 6.

Item 8. The display element described in above Item 7 further employing white scattering substances and electrolyte.

Effects Of The Invention

According to the present invention, electrochromic compounds exhibiting excellent memory characteristics and coloring stability over time, electrodes employing thereof, and display elements employing the aforementioned electrode could be provided.

DESCRIPTION OF THE PREFERRED EMBODIMENTS

Figure 1:
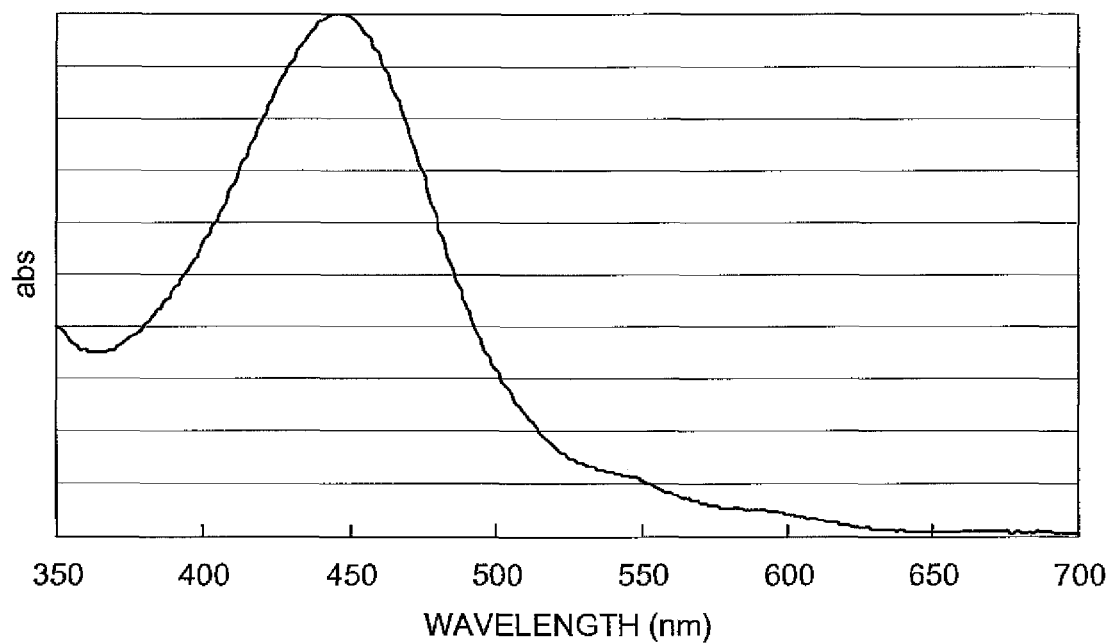
FIG. 1: Absorption spectrum of Example of Compound 1-1 in the oxidation state

In view of the foregoing, the inventors carried out a diligent examination, and as a result, the inventors found that, by introducing a functional silane (a hydrolysable group such as an alkoxysilane or halosilane) as a substituent into an electrochromic compound exhibiting a specific structure, it is possible to provide electrochromic compounds exhibiting excellent memory characteristics and coloring stability over time. Thus the present invention could be completed.

The present invention will be described in details below.

The electrochromic compounds represented by above-described Formula (1) of the present invention are described below. The electrochromic compounds are compounds which exhibit an electrochromic phenomenon, and the electrochromic phenomenon is a phenomenon which changes electron transfer energy in a visible region to result in a change in color of substances by electrically or electrochemically controlling oxidation reduction reactions of substances.

In Formula (1), $R_1$ represents an alkyl group (for example, a methyl group, an ethyl group, a propyl group, an isopropyl group, a t-butyl group, a pentyl group, a hexyl group, an octyl group, a dodecyl group, a tridecyl group, a tetradecyl group, or a pentadecyl group, a chloromethyl group, a trifluoromethyl group, a trichloromethyl group, a tribromomethyl group, a pentafluoroethyl group, or a methoxyethyl group), an alkenyl group (for example, a vinyl group, a allyl group, a butenyl group, or a octenyl group), an aryl group (for example, a phenyl group, a naphthyl group, a p-tolyl group, a m-chlorophenyl group, or an o-hexadecanoyl aminophenyl group), a heterocyclic group (for example, a pyridyl group, a thiazolyl group, an oxazolyl group, an imidazolyl group, a furyl group, a pyrrolyl group, a pyrazinyl group, a pyrimidinyl group, a pyridazinyl group, a selenazolinyl group, a sulfolanyl group, a piperidinyl group, a pyrazolyl group, a tetrazolyl group, or a morpholino group). Of these, $R_1$ is preferably an aryl group, and more preferably a phenyl group.

In Formula (1), an alkyl group, an alkenyl group, an aryl group, or a heterocyclic group, all of which are represented by $R_1$, may further have a substituent, and the substituent includes a halogen atom (for example, a fluorine atom, a chlorine atom, a bromine atom, or an iodine atom), an alkyl group (for example, a methyl group, an ethyl group, a propyl group, an isopropyl group, a t-butyl group, a pentyl group, a hexyl group, an octyl group, a dodecyl group, a tridecyl group, a tetradecyl group, a pentadecyl group, a chloromethyl group, a trifluoromethyl group, a trichloromethyl group, a tribromomethyl group, a pentafluoroethyl group, or a methoxyethyl group), a cycloalkyl group (for example, a cyclopentyl group or a cyclohexyl group), an alkenyl group (for example, a vinyl group or a allyl group), an alkinyl group (for example, an ethynyl group, or propargyl group), an aryl group (for example, a phenyl group, a naphthyl group, a p-nitrophenyl group, a p-fluorophenyl group, or a p-methoxyphenyl group), a heterocyclic group (for example, a furyl group, a thienyl group, a pyrizyl group, a pyridazyl group, a pyrimidyl group, a pyrazyl group, a triazyl group, an imidazolyl group, a pyrazolyl group, a thiazolyl group, a benzimidazolyl group, a benzoxazolyl group, a quinazolyl group, a phthalazyl group, a pyrrolidyl group, an imidazolidyl group, a morpholyl group, or an oxazolidyl group), a hydroxyl group, an alkoxy group (for example, a methoxy group, an ethoxy group, a propyoxy group, an isopropyoxy group, a butoxy group, a t-butoxy group, or a sec-butoxy group) an alkoxycarbonyl group (for example, a methyloxycarbonyl group, an ethyloxycarbonyl group, a butyloxycarbonyl group, an octyloxycarbonyl group, or a dodecyloxycarbonyl group), an aryloxycarbonyl group (for example, a phenyloxycarbonyl group, or a naphthyloxycarbonyl group), a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, or a 2-pyridylaminosulfonyl group), an acyl group (for example, an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, or a pyridylcarbonyl group), a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl group, a phenylaminocarbonyl group, a naphthylaminocarbonyl group, or a 2-pyridylaminocarbonyl group), a sulfinyl group (for example, a methylsulfinyl group, an ethylsulfinyl group, a butylsulfinyl group, a cyclohexylsulfinyl group, a 2-ethylhexylsulfinyl group, a dodecylsulfinyl group, a phenylsulfinyl group, a naphthylsulfinyl group, or a 2-pyridylsulfinyl group), an alkylsulfonyl group (for example, a methylsulfonyl group, an ethylsulfonyl group, a butylsulfonyl group, a cyclohexylsulfonyl group, a 2-ethylhexylsulfonyl group, or a dodecylsulfonyl group), an arylsulfonyl group (for example, a phenylsulfonyl group, a naphthylsulfonyl group, or a 2-pyridylsulfonyl group), a cyano group, an amino group (for example, an amino group, a methylamino group, a dimethylamino group, an ethylamino group, a diethylamino group, a butylamino group, or a dibutylamino group), an acylamino group (for example, an acetamide group, a propioamide group, isopropioamide group, a butanamide group, or a pivaloylamide group). Of these, the substituent is preferably a hydroxyl group, an alkyl group, an alkoxy group, or an acylamino group, and more preferably a hydroxyl group, or an alkyl group. Preferable alkyl group includes a methyl group, a t-butyl group, or a t-octyl group.

In Formula (1) each of $R_2$ and $R_3$ represents a substituent, and the substituent includes a halogen atom (for example, a fluorine atom, a chlorine atom, a bromine atom, or an iodine atom), an alkyl group (for example, a methyl group, an ethyl group, a propyl group, an isopropyl group, a t-butyl group, a pentyl group, a hexyl group, an octyl group, a dodecyl group, a tridecyl group, a tetradecyl group, a pentadecyl group, a chloromethyl group, a trifluoromethyl group, a trichloromethyl group, a tribromomethyl group, a pentafluoroethyl group, or a methoxyethyl group), a cycloalkyl group (for example, a cyclopentyl group or a cyclohexyl group), an alkenyl group (for example, a vinyl group or a allyl group), an alkinyl group (for example, an ethynyl group, or propargyl group), an aryl group (for example, a phenyl group, a naphthyl group, a p-nitrophenyl group, a p-fluorophenyl group, or a p-methoxyphenyl group), a heterocyclic group (for example, a furyl group, a thienyl group, a pyrizyl group, a pyridazyl group, a pyrimidyl group, a pyrazyl group, a triazyl group, an imidazolyl group, a pyrazolyl group, a thiazolyl group, a benzimidazolyl group, a benzoxazolyl group, a quinazolyl group, a phthalazyl group, a pyrrolidyl group, an imidazolidyl group, a morpholyl group, or an oxazolidyl group), an alkoxy group (for example, a methoxy group, an ethoxy group, a propyoxy group, an isopropyoxy group, a butoxy group, a t-butoxy group, or a sec-butoxy group), an alkoxycarbonyl group (for example, a methyloxycarbonyl group, an ethyloxycarbonyl group, a butyloxycarbonyl group, an octyloxycarbonyl group, or a dodecyloxycarbonyl group), an aryloxycarbonyl group (for example, a phenyloxycarbonyl group, or a naphthyloxycarbonyl group), a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, or a 2-pyridylaminosulfonyl group), an acyl group (for example, an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecycarbonyl group, a phenylcarbonyl group, a naphthylcarbonyl group, or a pyridylcarbonyl group), a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl group, a phenylaminocarbonyl group, a naphthylaminocarbonyl group, or a 2-pyridylaminocarbonyl group), a sulfinyl group (for example, a methylsulfinyl group, an ethylsulfinyl group, a butylsulfinyl group, cyclohexylsulfinyl group, a 2-ethylhexylsulfinyl group, a dodecylsulfinyl group, a phenylsulfinyl group, a naphthylsulfinyl group, or a 2-pyridylsulfinyl group), an alkylsulfonyl group (for example, a methylsulfonyl group, an ethylsulfonyl group, a butylsulfonyl group, a cyclohexylsulfonyl group, a 2-ethylhexylsulfonyl group, or a dodecylsulfonyl group), an arylsulfonyl group (for example, a phenylsulfonyl group, a naphthylsulfonyl group, or a 2-pyridylsulfonyl group), a cyano group, an amino group (for example, an amino group, a methylamino group, a dimethylamino group, an ethylamino group, a diethylamino group, a butylamino group, or a dibutylamino group), an acylamino group (for example, an acetamide group, a propioamide group, isopropioamide group, a butanamide group, or a pivaloylamide group). Of these, preferable substituent is hydrogen atom, an alkyl group, an aryl group, a heterocyclic group, or an amino group, and more preferably an aryl group, or a heterocyclic group. Preferable aryl group is a phenyl group, and preferable heterocyclic group is a furyl group, a thienyl group, or a pyridyl group, and more preferable heterocyclic group is a thienyl group. Further, $R_2$ and $R_3$ may be combined each other to form a ring.

In Formula (1), X represents $N-R_4$, an oxygen atom, or a sulfur atom, preferably $N-R_4$, or an oxygen atom, and more preferably $N-R_4$.

$R_4$ represents a hydrogen atom, or a substituent, and preferably a hydrogen atom. The substituent preferably includes an alkyl group (for example, a methyl group, an ethyl group, a propyl group, an isopropyl group, a t-butyl group, a pentyl group, a hexyl group, an octyl group, a dodecyl group, a tridecyl group, a tetradecyl group, a pentadecyl group, a chloromethyl group, a trifluoromethyl group, a trichloromethyl group, a tribromomethyl group, a pentafluoroethyl group, or a methoxyethyl group), an aryl group (for example, a phenyl group, a naphthyl group, a p-nitrophenyl group, a p-fluorophenyl group, or a p-methoxyphenyl group), a heterocyclic group (for example, a furyl group, a thienyl group, a pyrizyl group, a pyridazyl group, a pyrimidyl group, a pyrazyl group, a triazyl group, an imidazolyl group, a pyrazolyl group, a thiazolyl group, a benzimidazolyl group, a benzoxazolyl group, a quinazolyl group, a phthalazyl group, a pyrrolidyl group, an imidazolidyl group, a morpholyl group, or an oxazolidyl group), an acyl group (for example, an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecycarbonyl group, a phenylcarbonyl group; a naphthylcarbonyl group, or a pyridylcarbonyl group), and preferably an alkyl group, or an aryl group. The alkyl group preferably includes a butyl group, a pentyl group, a hexyl group, or an octyl group. The Aryl group preferably includes a phenyl group.

The electrochromic compound represented by Formula (1) can electrically exhibit an oxidation-reduction reaction, but any compound may be employed as long as either an oxidized form or a reduced form of the compound exhibits a structure represented by Formula (1), and the structure of the reduction form is preferably represented by Formula (1).

At least one of $R_1$ to $R_4$ of the electrochromic compound represented by Formula (1) of the present invention exhibits above Formula (2) as a partial structure.

In Formula (2), Y represents a halogen atom (for example, a fluorine atom, a chlorine atom, a bromine atom, or an iodine atom), or OR, and preferably OR. As the halogen atom, a chlorine atom is preferred.

R represents an alkyl group (for example, a methyl group, an ethyl group, a propyl group, an isopropyl group, a t-butyl group, a pentyl group, a hexyl group, an octyl group, a dodecyl group, a tridecyl group, a tetradecyl group, a pentadecyl group, a chloromethyl group, a trifluoromethyl group, a trichloromethyl group, a tribromomethyl group, a pentafluoroethyl group, or a methoxyethyl group), or an aryl group (for example, a phenyl group, a naphthyl group, a p-tolyl group, a m-chlorophenyl group, or a o-hexadecanoyl aminophenyl group). R is preferably an alkyl group, and more preferably a methyl group or an ethyl group.

In Formula (2), R' represents an alkyl group (for example, a methyl group, an ethyl group, a propyl group, an isopropyl group, a t-butyl group, a pentyl group, a hexyl group, an octyl group, a dodecyl group, a tridecyl group, a tetradecyl group, a pentadecyl group, a chloromethyl group, a trifluoromethyl group, a trichloromethyl group, a tribromomethyl group, a pentafluoroethyl group, or a methoxyethyl group), an alkenyl group (for example, a vinyl group or a allyl group), an aryl group (for example, a phenyl group, a naphthyl group, a p-nitrophenyl group, a p-fluorophenyl group, or a p-methoxyphenyl group), a heterocyclic group (for example, a furyl group, a thienyl group, a pyrizyl group, a pyridazyl group, a pyrimidyl group, a pyrazyl group, a triazyl group, an imidazolyl group, a pyrazolyl group, a thiazolyl group, a benzimidazolyl group, a benzoxazolyl group, a quinazolyl group, a phthalazyl group, a pyrrolidyl group, an imidazolidyl group, a morpholyl group, or an oxazolidyl group). R' is preferably an alkyl group, or an aryl group, and more preferably an alkyl group. The alkyl group preferably includes a methyl group, or an ethyl group, and more preferably a methyl group.

n represents an integer, and in case where Y is a halogen atom, n is preferably 1 or 2, and more preferably n is 1. In case where Y is OR, n is preferably 2 or 3, and more preferably n is 3.

Any functional silane (a hydrolysable group such as an alkoxysilane or halosilane) represented by Formula (2) of the present invention may be employed as long as it can form a silanol bond, and a trialkoxysilane compound or a trichlorosilane compound is preferred since they are readily synthesized. The trichlorosilane exhibits a high reactivity so that it can be easily absorbed in a short time into various metal oxides. The trialkoxysilane exhibits a relatively mild reactivity so that the progress of the reaction is readily controlled. Further, when a monochlorosilane compound or a monoalkoxysilane compound is employed, oligomerization thereof can be prevented, so that the amount of absorption into metal oxides is readily controlled.

Specific examples of the electrochromic compound represented by Formula (1) are listed below, but the present invention is not limited to these illustrated compounds.

1-1

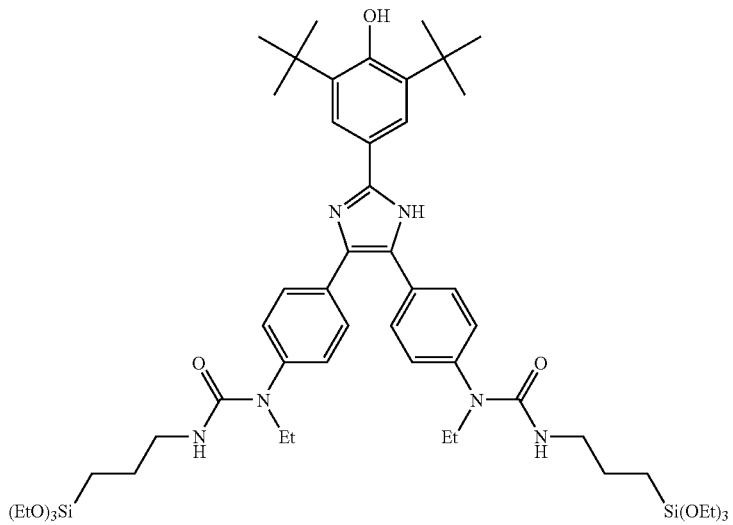

1-2

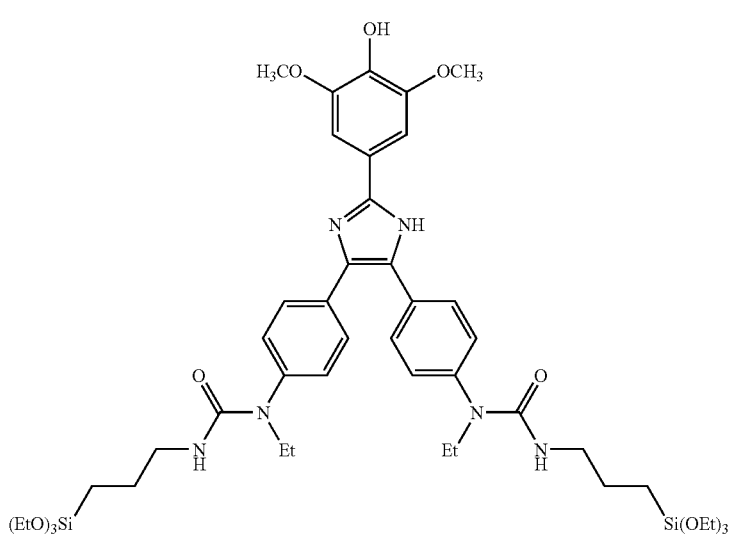

-continued
1-3
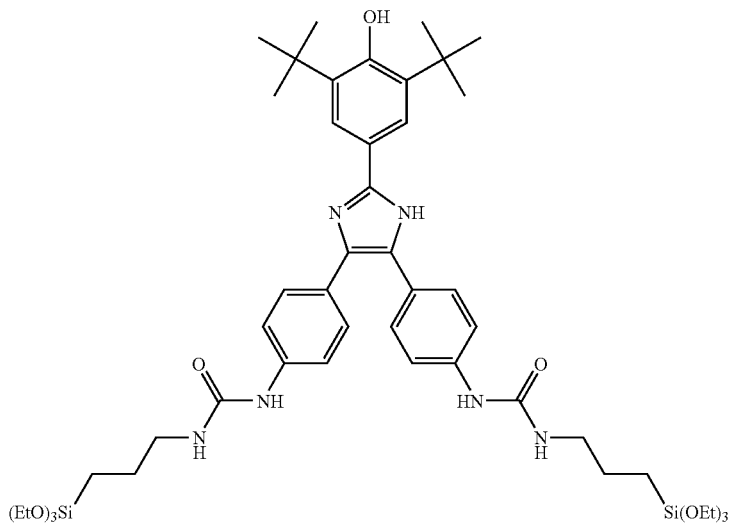
1-4
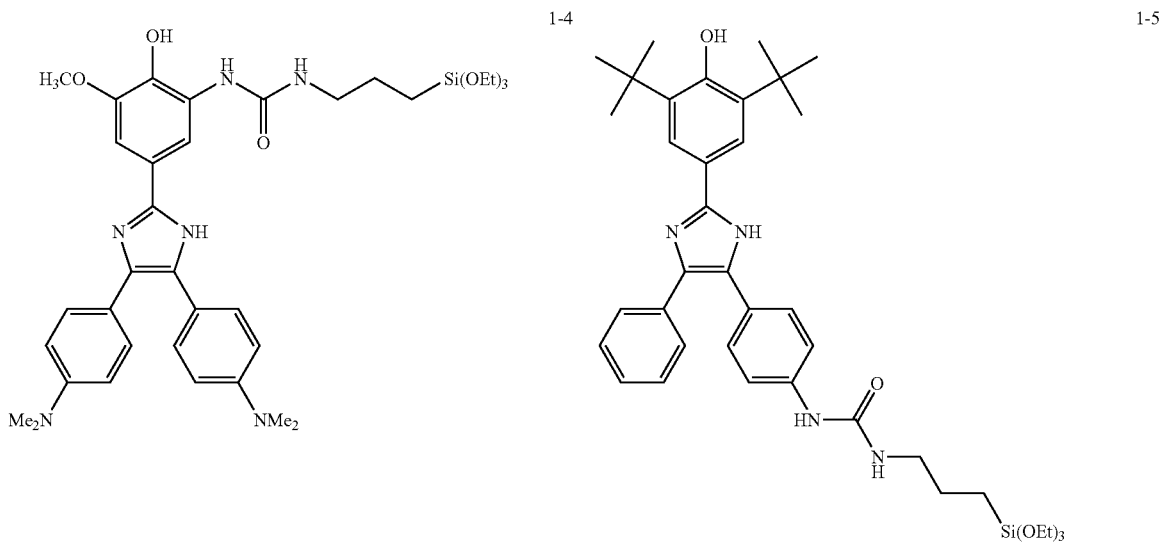
1-5
1-6
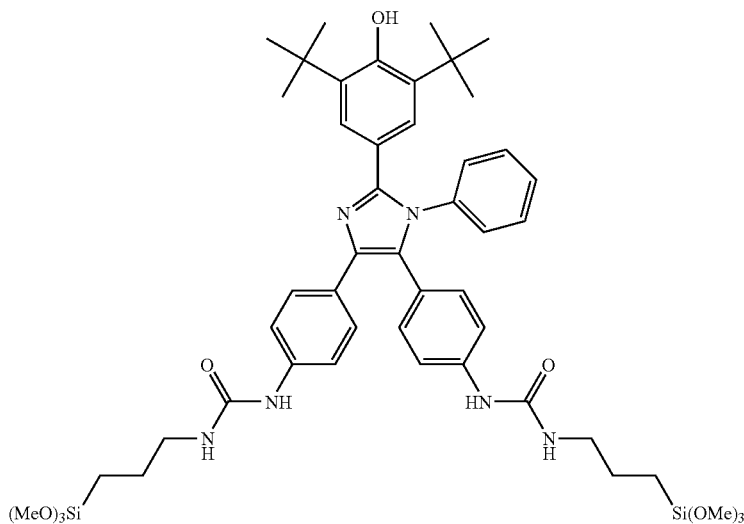

1-7
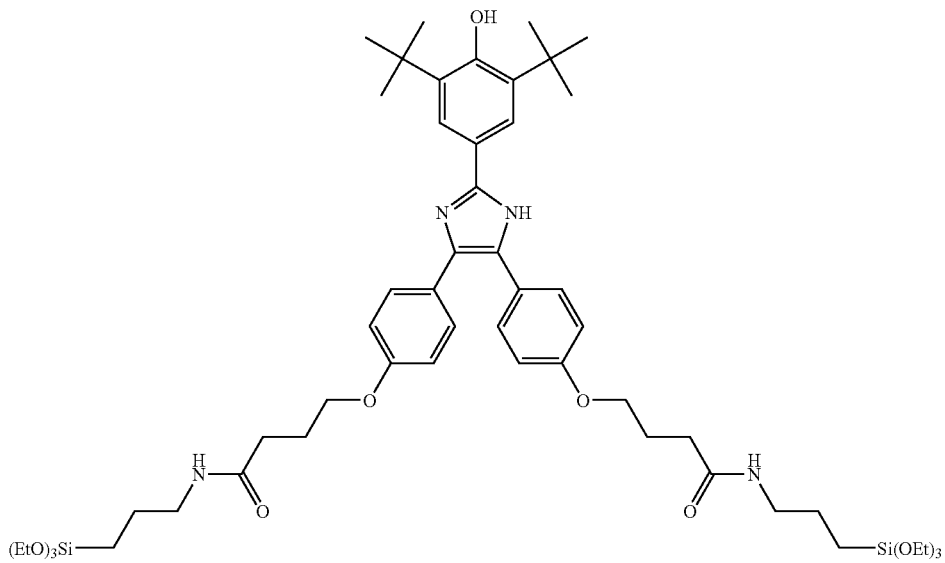
1-8
1-9
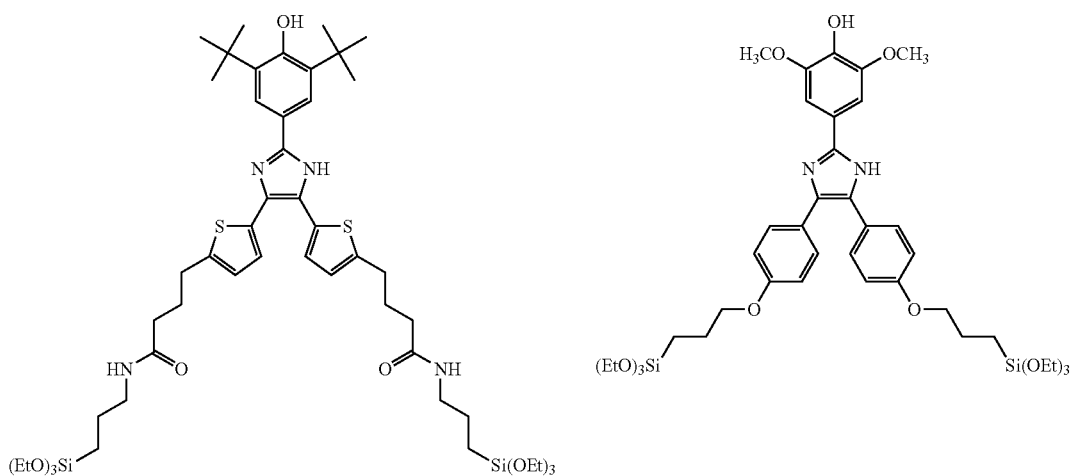
1-10
1-11
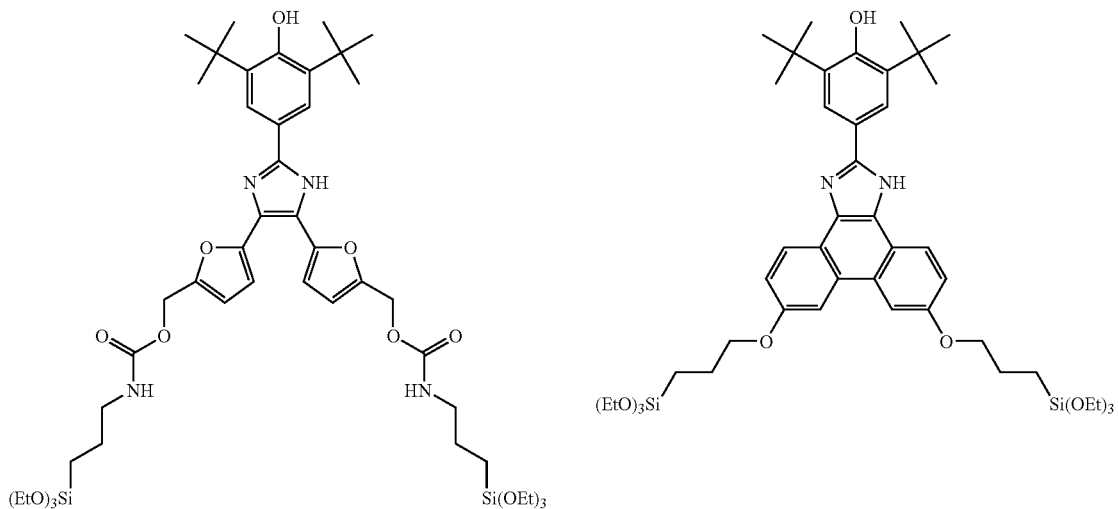

-continued
1-12
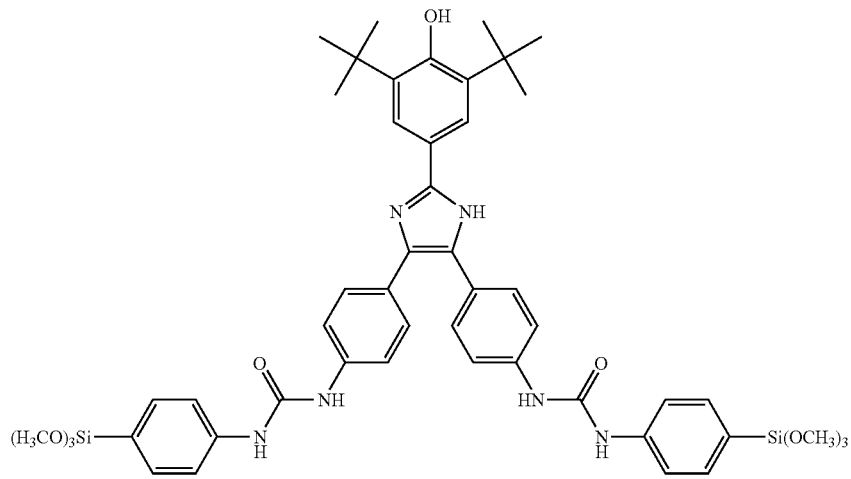
1-13
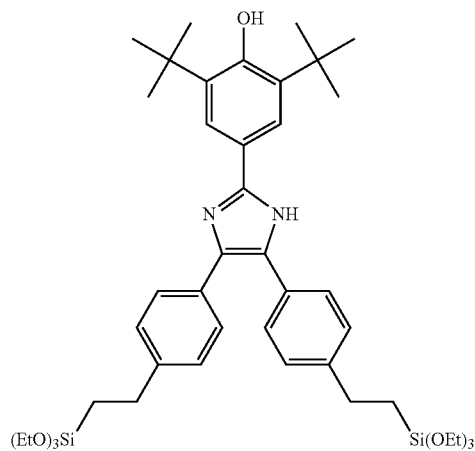
1-14
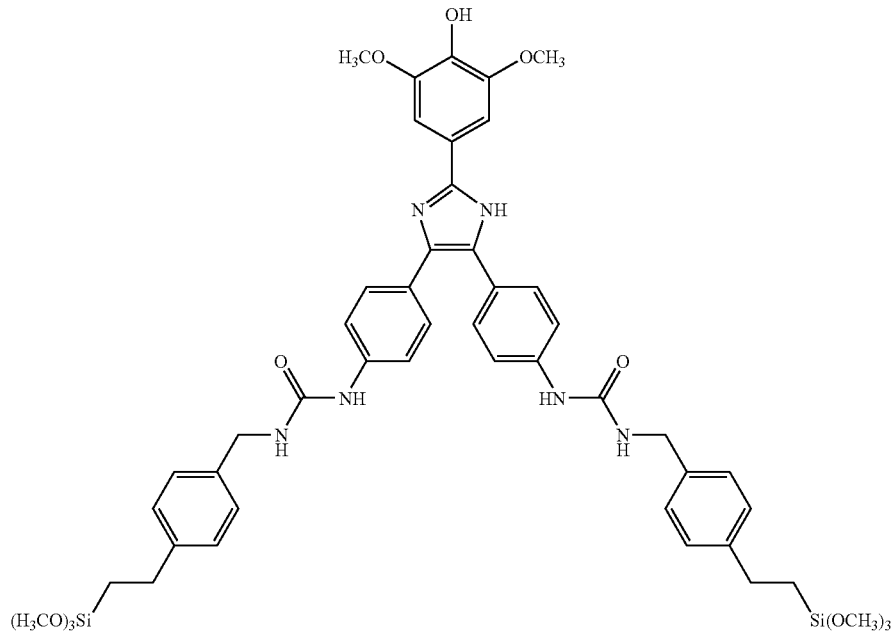

1-15
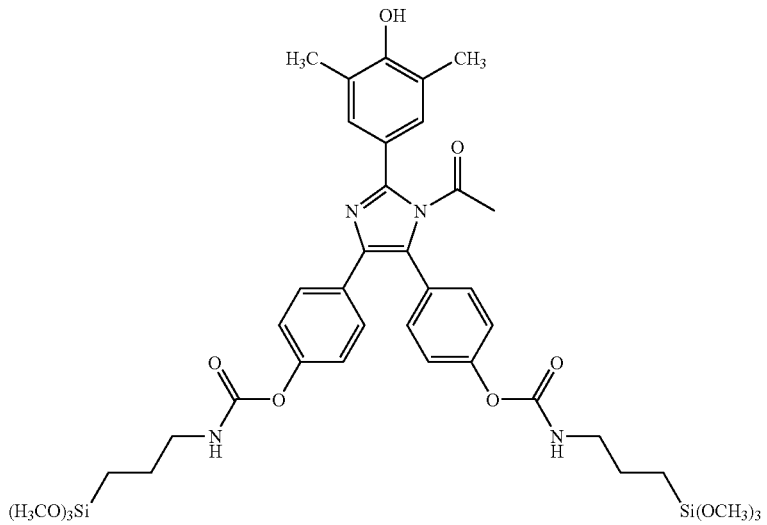
1-16
1-17
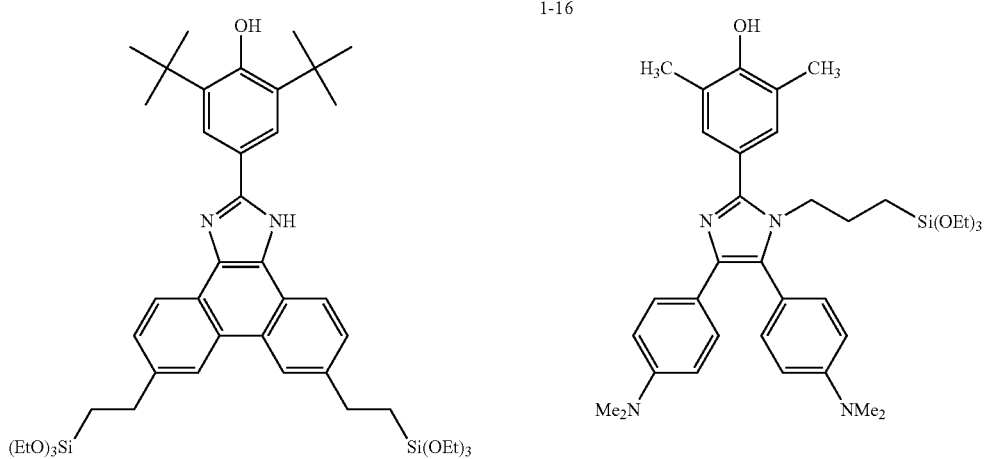
1-18
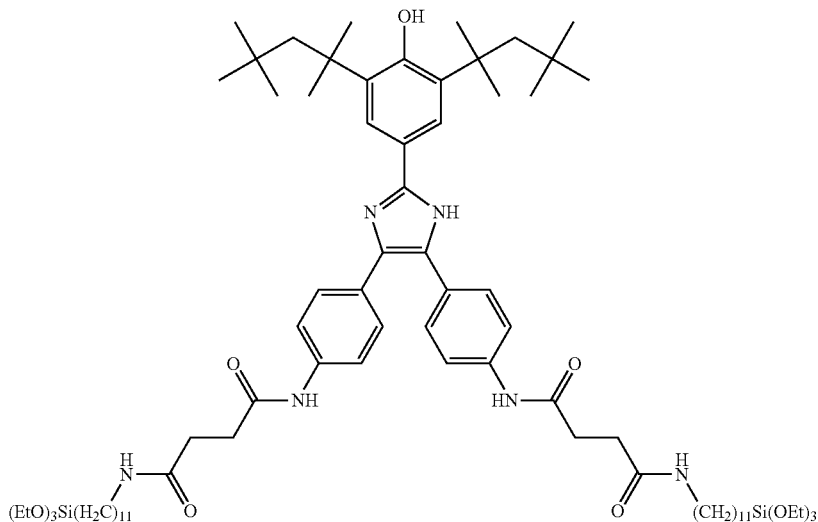

1-19
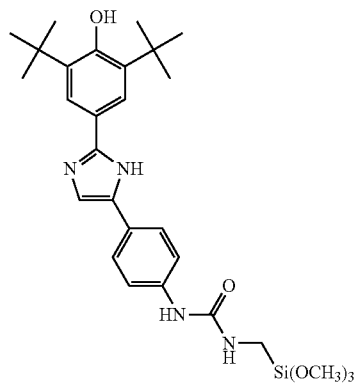
1-20
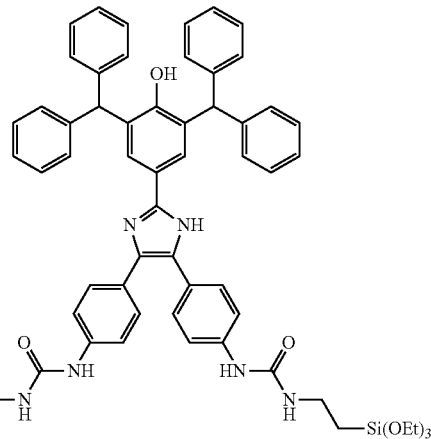
1-21
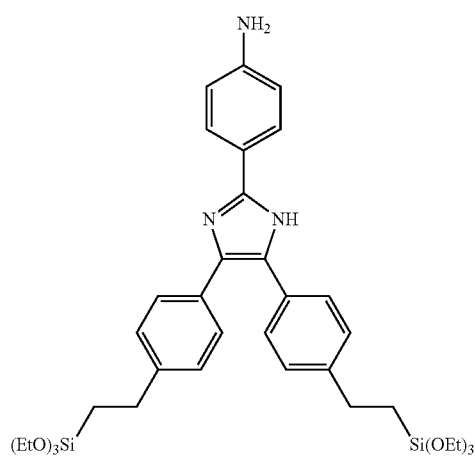
1-22
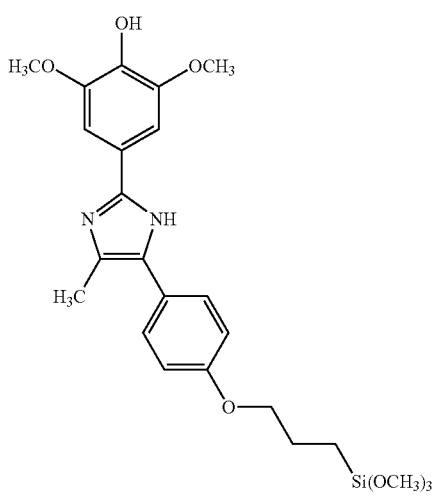
1-23
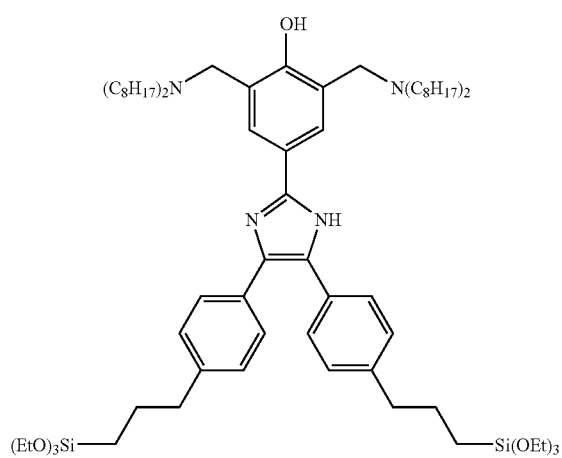

-continued
1-24
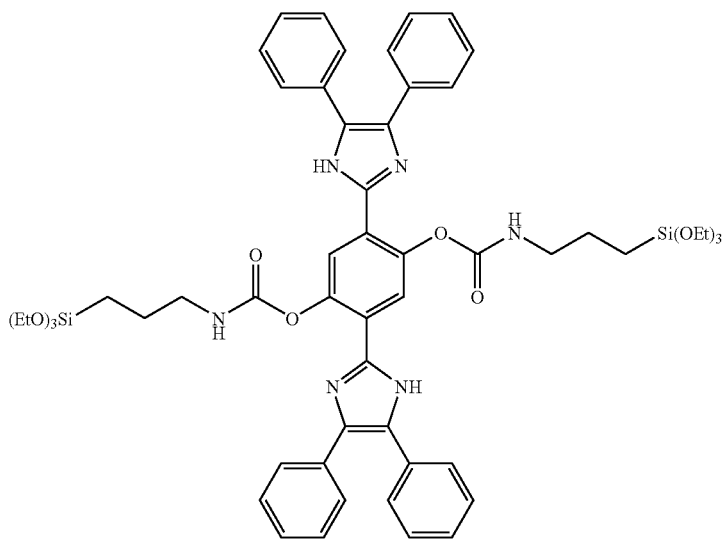
1-25
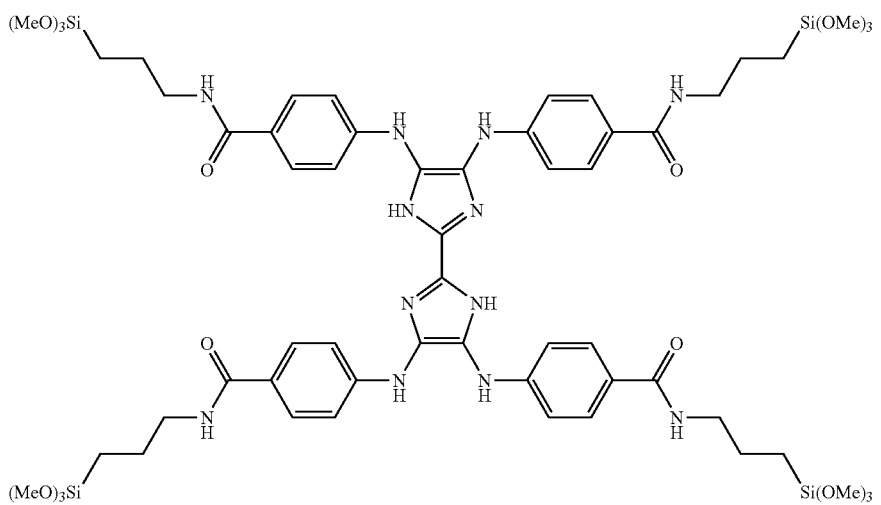
1-26
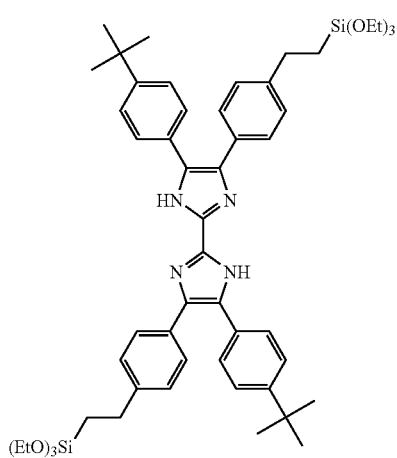
1-27
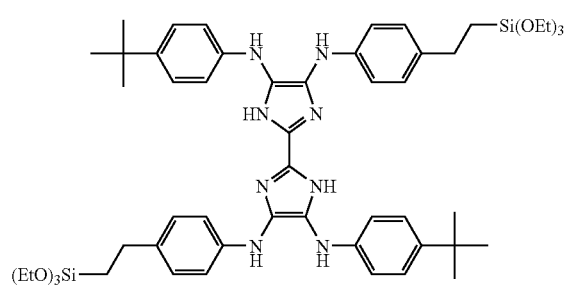

-continued
1-28
1-29
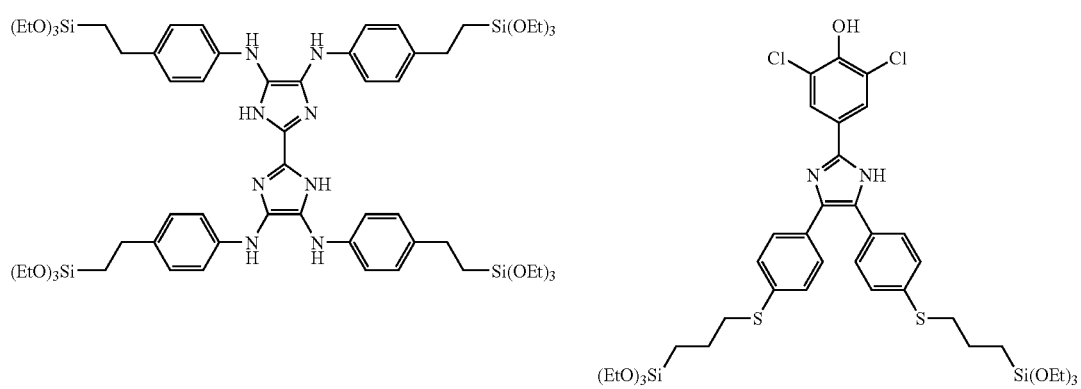
1-30
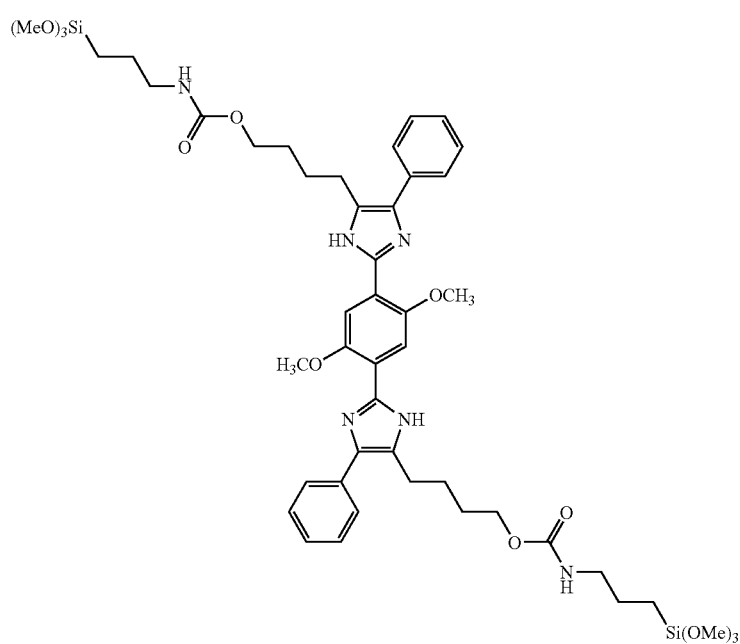
1-31
1-32
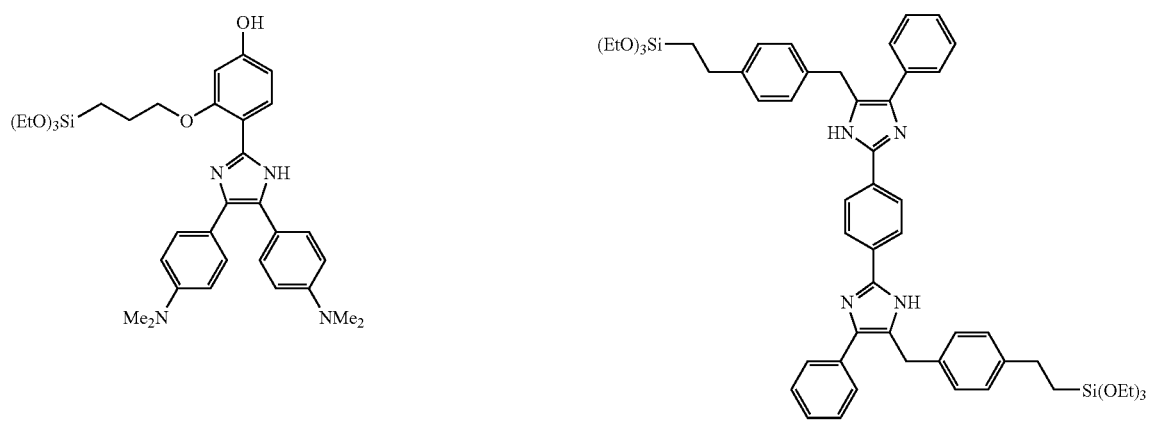

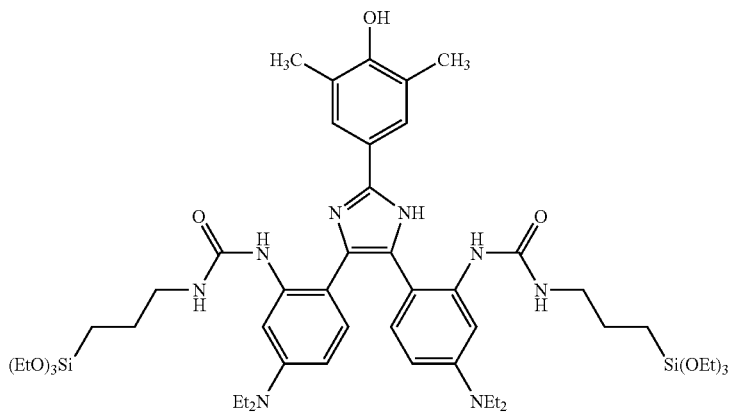
1-33
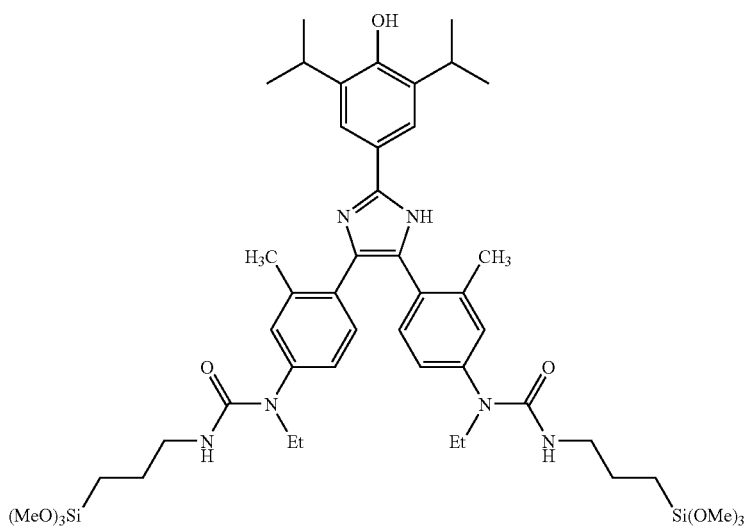
1-34
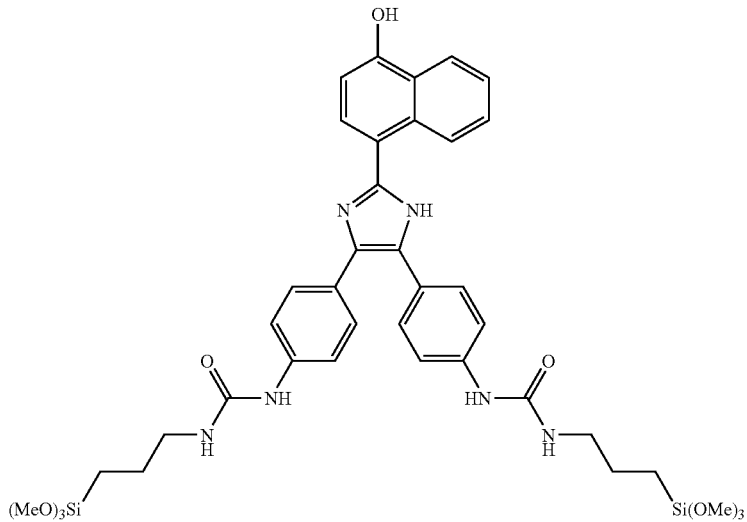
1-35

1-36
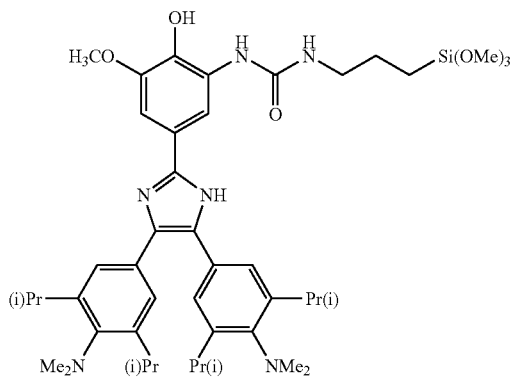
1-37
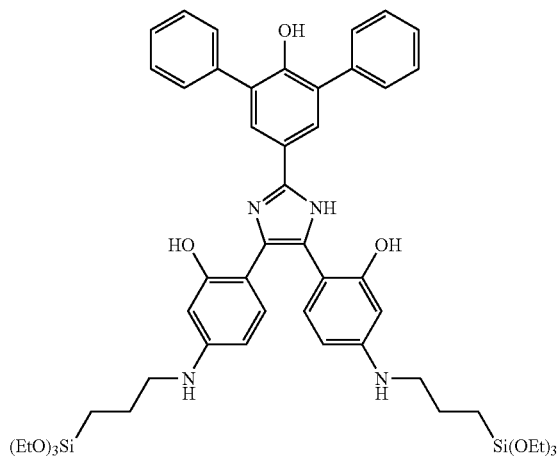
1-38
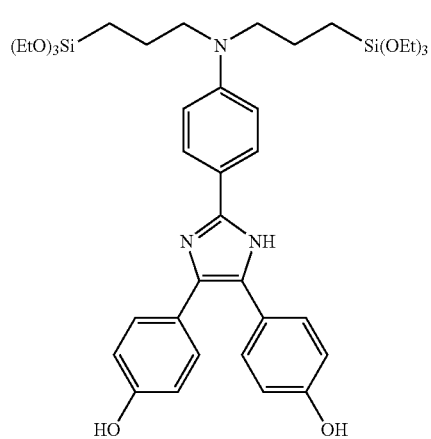
1-39
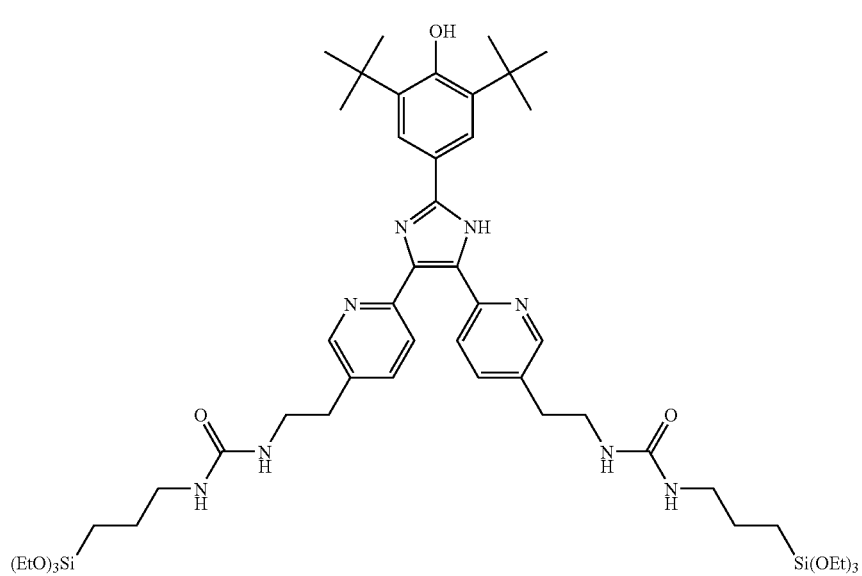

1-40
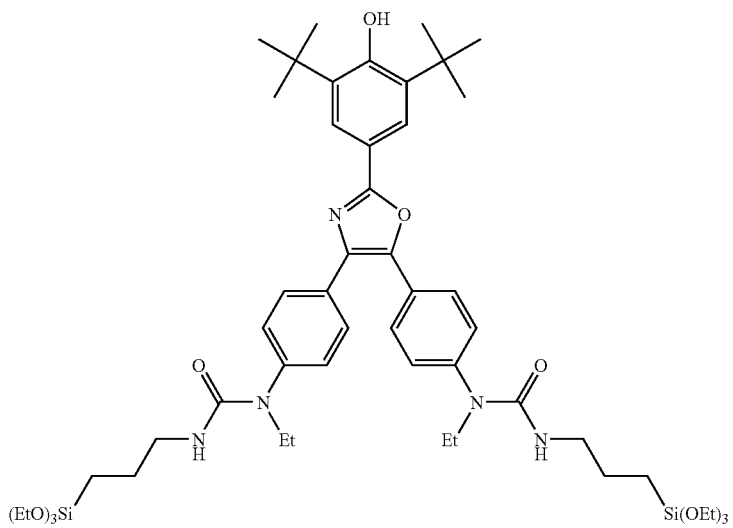
1-41
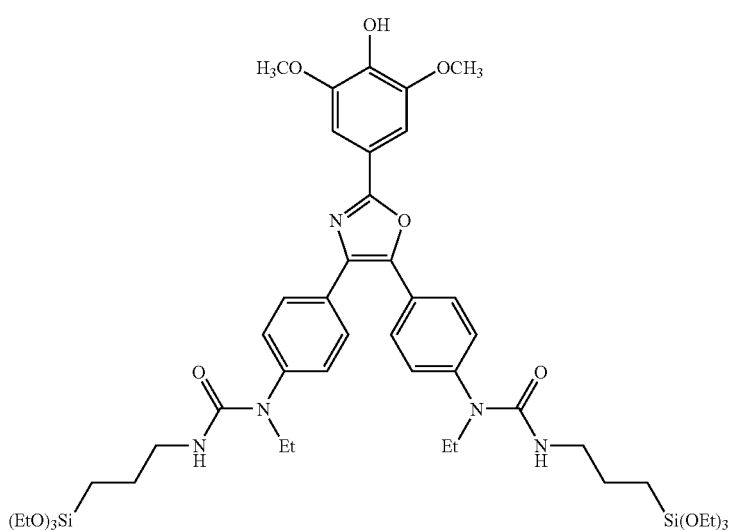
1-42
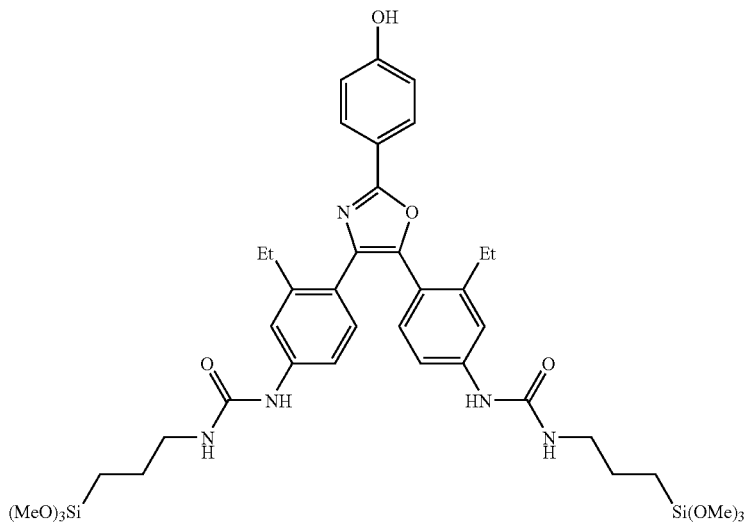

-continued
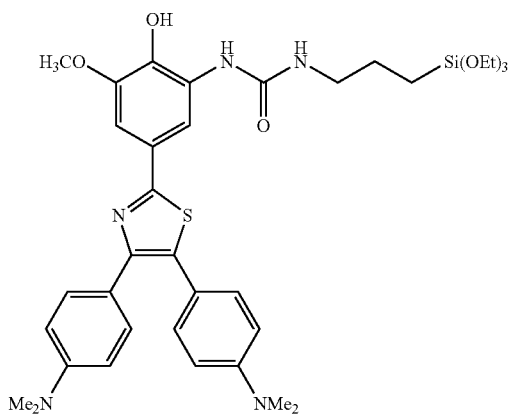
1-43
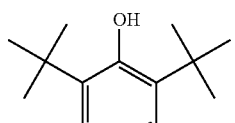
1-44
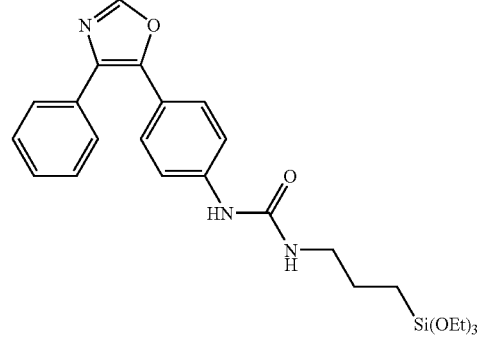
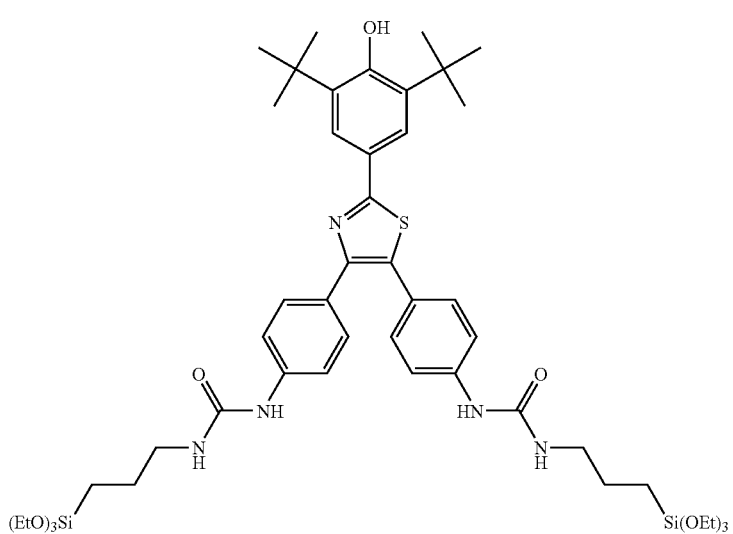
1-45
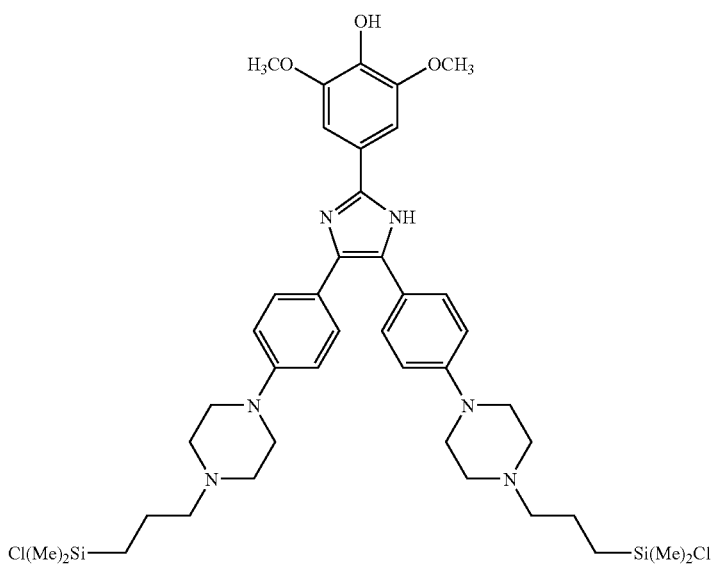
1-46

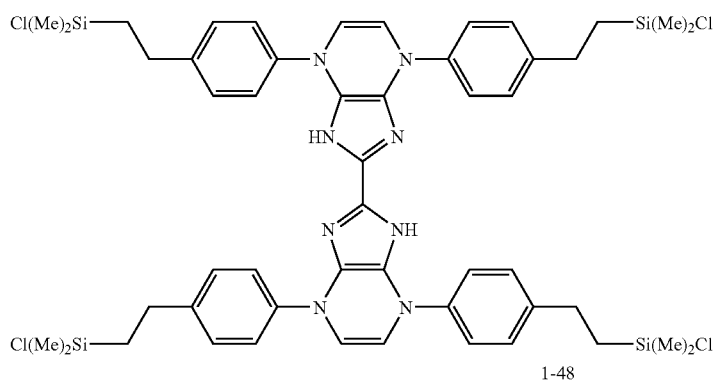

1-47

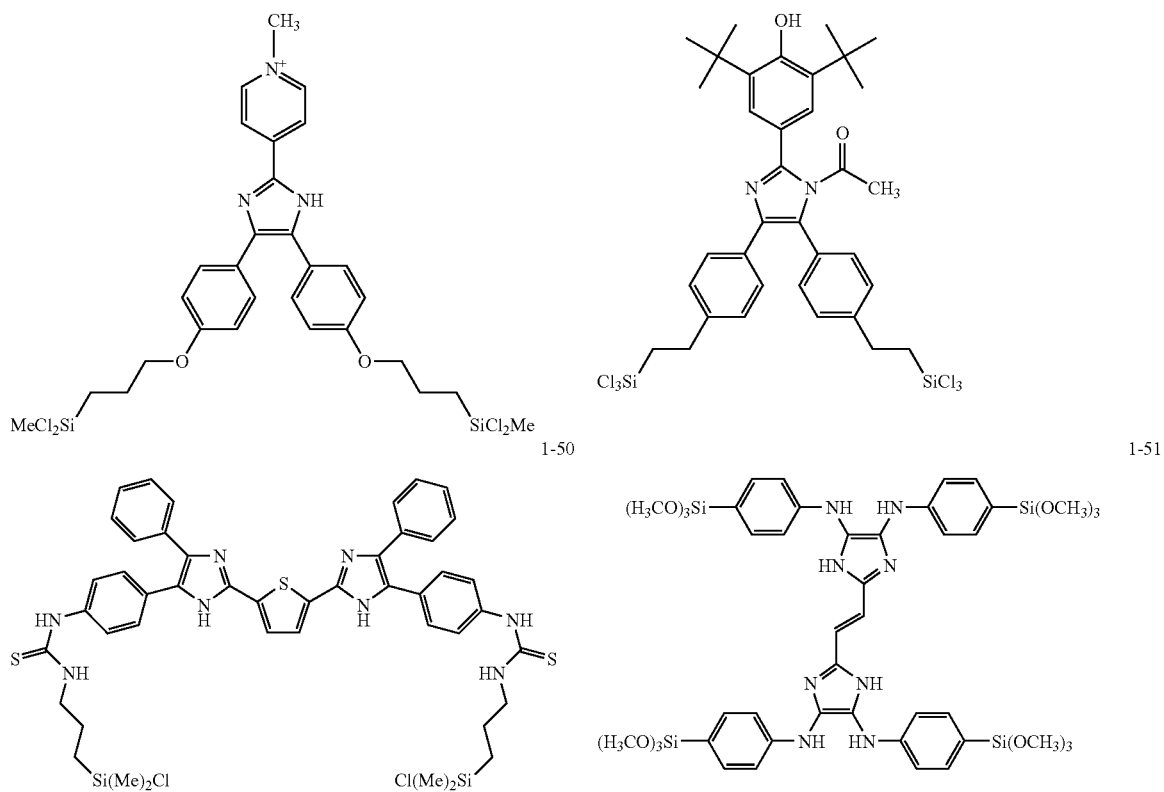

<<Electrode>>

In the present invention, the electrochromic compound represented by Formula (1) is characterized in that the aforesaid compound chemically binds to an electrode, and further the aforesaid electrode is preferably a transparent one.

The transparent electrode is not particularly limited as long as it is transparent and electrically conductive. Examples of the aforesaid transparent electrode include electrodes on which a layer is formed with substances such as indium tin oxide (ITO), indium zinc oxide (IZO), fluorine-doped tin oxide (FTO), indium oxide, zinc oxide, platinum, gold, silver, rhodium, cupper, chromium, carbon, aluminum, silicon, amorphous silicon, and BSO (Bismuth Silicone Oxide).

Above transparent electrodes may be formed in such a manner that, for example, an ITO film is mask-deposited on a substrate via methods such as a sputtering method, or an ITO film is formed all over a substrate, after which the substrate is subjected to a patterning via a photolithography method. The value of the surface resistivity is preferably 100 Ω/sq. or less, and more preferably 10 Ω/sq. or less. The thickness of the transparent electrode is not particularly limited, but is generally 0.1 to 20 μm.

Methods for chemically binding electrochromic compound represented by Formula (1) of the present invention on the electrode include, for example, a method which directly combines the electrochromic compound represented by Formula (1) with an electrode through a silanol bond, and a method which forms a porous layer comprising a metal oxide on an electrode, and combines the electrochromic compound represented by Formula (1) with the electrode through a silanol bond with the metal oxide, and preferred is a method which combines the electrochromic compound with the electrode through a porous layer comprising a metal oxide.

It is assumed that the reason of degradation with age of properties of absorption which has, in the past, utilized a terminal of an acid group such as a phosphoric acid or a carboxylic acid is that the absorption is not so strong that desorption of the electrochromic compounds from inorganic fine particles occurs. In contrast, it is assumed that, by allowing the electrochromic compounds of the present invention to bind to the metal oxide through the silanol bond, exhibiting a strong bonding strength, desorption of the electrochromic materials scarcely occurs with age to result in excellent coloring stability over time. Further, since the electrochromic compounds of the present invention exhibit different absorption state from absorptions which has, in the past, utilized a terminal of an acid group such as a phosphoric acid or a carboxylic acid, memory characteristics are assumed to be improved due to changes in the electron state.

As a substrate which is usable for the electrode in the present invention, synthetic plastic films are also preferably employed. Examples of the above film include polyolefins such as polyethylene and polypropylene, polycarbonates, cellulose acetate, polyethylene terephthalate, polyethylene dinaphthalene dicarboxylate, polyethylene naphthalates, polyvinyl chloride, polyimide, polyvinyl acetals, and polystyrene. Polystyrenes with a syndiotactic structure are also preferable.

These substrates can be obtained according to the methods described, for example, in each of publications of JP-A Nos. 62-117708, 1-46912, and 1-178505. In addition, the substrate also includes metal substrates such as stainless steel, a baryta paper, paper supports such as a resin-coated paper, supports which has a reflection layer provided on the above plastic films, and supports described in JP-A 62-253195 (on pages 29-31). Supports described on page 28 of Research Disclosure (hereinafter, referred to as RD) No. 17643, in the right column of page 647 to the left column of page 648 of RD No. 18716, and on page 879 of RD No. 307105 are also preferably employed.

For these supports, usable are supports which are made to exhibit less core set by heat treatment at temperature of Tg or less, as described in U.S. Pat. No. 4,141,735. Further, the surface of the above supports may be subjected to a surface treatment with the aim of enhancement of adhesion between the support and other constituting layers. In the present invention, the surface treatment can be performed by a glow discharge treatment, an ultraviolet ray irradiation treatment, a corona treatment, or a flame treatment. In addition, supports described on pages 44-149 of Kochi Gijutsu (Prior Art Technology) No. 5 (published by AZTEC Corp., dated Mar. 22, 1991) may be employed. Further, listed are those described on page 1009 of RD No. 308119, as well as in the item "Supports" on page 108 of Product Licensing Index, Volume 92. Other than the above, glass substrates as well as epoxy resins kneaded with glass powder may be employed.

<<Display Element>>

Since coloring and discoloring of the electrochromic compounds represented by Formula (1) of the present invention can be electrochemically carried out, electrodes, on which chemical bonds of the electrochromic compounds represented by Formula (1) of the present invention are formed, can be utilized as display materials. Further, the above compounds can be utilized as full color display materials exhibiting reversible memory characteristics by electrochemically repeating coloring and discoloring.

Figure 6:
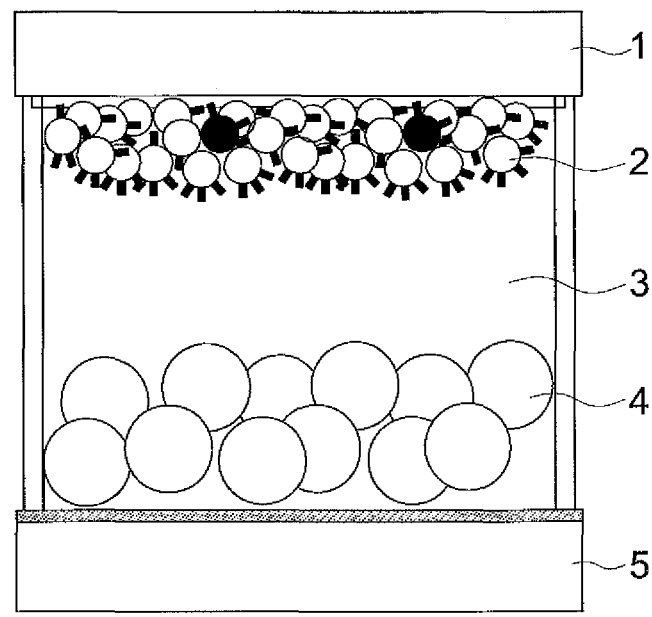
FIG. 6: Schematic diagram of the display element of the present invention

An example of how the above materials are used is described below. As shown in FIG. 6, in display elements composed of an electrode, a display layer, electrolytes, a white scattering layer and a counter electrode, a layer, in which the electrochromic compound of the present invention is allowed to react with porous substances comprising metal oxides such as titanium oxides, is employed as the display layer, and by applying voltage of both positive and negative polarities between counter electrodes, the electrochromic compound is subjected to an oxidation and reduction, and then, a colored display and a white display can be achieved by utilizing a difference in colors between at an oxidation state and at a reduction state, as well as the white scattering layer arranged between electrodes.

(Electrolyte)

In general, the term "an electrolyte" indicates a substance which is dissolved in solvents such as water so that the resulting solution exhibits an ion conductivity (hereinafter, referred to as "an electrolyte in a narrow sense), but "an electrolyte" used in the present invention indicates a mixed compound in which other substance such as a metal or a compound, whether it is an electrolyte or a nonelectrolyte, is incorporated into the electrolyte in a narrow sense (referred to as "an electrolyte in a broad sense").

In the display element of the present invention, in case where the electrolyte is liquid, electrolyte solvents are usable. Examples thereof include tetramethylurea, sulfolane, dimethyl sulfoxide, 1,3-dimethyl-2-imidazolidinone, 2-(N-methyl)-2-pyrrolidinone, hexamethylphosphortriamide, N-methylpropioneamide, N,N-dimethylacetamide, N-methylacetamide, N,N-dimethlylformamide, N-methylformamide, butyronitrile, propionitrile, acetonitrile, acetylacetone, 4-methyl-2-pentanone, 2-butanol, 1-butanol, 2-propanol, 1-propanol, ethanol, methanol, acetic anhydride, ethyl acetate, ethyl propionate, dimethoxy ethane, diethoxyfuran, tetrahydrofuran, ethylene glycol, diethylene glycol, triethylene glycol monobutyl ether, ethylene carbonate, propylene carbonate, dimethyl carbonate, diethyl carbonate, methylethyl carbonate, γ-butyrolactone, dioxolan, sulfolane, and water. Of these solvents, at least one solvent exhibiting the freezing point of −20° C. or lower, and the boiling point of 120° C. or higher is preferably contained.

Other solvents usable in the present invention include compounds described in J. A. Riddick, W. B. Bunger, T. K. Sakano, "Organic Solvents", 4th ed., John Wiley & Sons (1986), Y. Marcus, "Ion Solvation", John Wiley & Sons (1985), C. Reichardt, "Solvents and Solvent Effects in Chemistry", 2nd ed., VCH (1988), G. J. Janz, R. P. T. Tomkins, and "Nonaqueous Electrolytes Handbook", Vol. 1, Academic Press (1972).

In the present invention, the electrolyte solvent may be one kind or a mixture of solvents, but a mixed solvent containing ethylene carbonate is preferred. An amount to be added of the ethylene carbonate is preferably 10% by mass or more, and 90% by mass or less based on the total amount of the electrolyte solvent. The electrolyte solvents, exhibiting the mass ratio of propylene carbonate to ethylene carbonate being 7:3 to 3:7, is particularly preferred. In case where the ratio of the propylene carbonate is larger than 7:3, ion conductivity degrades to result in decrease in response speed, and in case where it is smaller than 3:7, the electrolytes tend to be precipitated at a low temperature.

In the present invention, solid electrolytes may be employed as the electrolyte. Polymers employed in these solid electrolytes include polyvinylidene fluoride series polymers such as polyvinylidene fluoride, vinylidene fluoride-hexafluoropropylene copolymer, vinylidene fluoride-ethylene copolymer, vinylidene fluoride-monofluoroethylene copolymer, and vinylidene fluoride-hexafluoropropylene-tetrafluoropropylene three-component copolymer; acrylonitrile series polymers such as acrylonitrile-methyl methacrylate copolymer, acrylonitrile-methyl acrylate copolymer, acrylonitrile-ethyl methacrylate copolymer, acrylonitrile-ethyl acrylate copolymer, acrylonitrile-methacrylic acid copolymer, acrylonitrile-acrylic acid copolymer, and acrylonitrile-vinyl acetate copolymer; as well as polyethylene oxide, ethylene oxide-propylene oxide copolymer, and acrylate polymers and methacrylate polymers of these compounds. These polymers may be employed as gel-like materials by adding electrolyte solution therein, or may be employed as they are.

(White Scattering Layer)

In the present invention, in view of more enhancing the display contrast and the reflectivity of the white display, white scattering substances are preferably incorporated, and a porous white scattering layer may be allowed to be formed and is incorporated.

The porous white scattering layer applicable to the present invention can be formed by coating and drying an aqueous admixture of aqueous polymers, which are substantially insoluble in the electrolyte solvents, and white pigments.

White pigments applicable to the present invention include, for example, titanium dioxide (an anatase type or a rutile type), barium sulfate, calcium carbonate, aluminum oxide, zinc oxide, magnesium oxide, as well as zinc hydroxide, magnesium hydroxide, magnesium phosphate, magnesium hydrogenphosphate, alkaline earth metal salts, talc, kaolin, zeolite, acid clay, glass; and further include organic compounds such as polyethylene, polystyrene, acryl resins, ionomers, ethylene-vinyl acetate copolymer resins, benzoguanamine resins, urea-formalin resins, melamine-formalinresins, and polyamide resins. These materials may be used individually or in the form of a composite mixture, as well as in a state containing, in the particles, voids which alter the refractive index.

In the present invention, among above white particles, titanium dioxide, zinc oxide, or zinc hydroxide is preferably employed. Further, employable are titanium dioxide which has been subjected to a surface treatment employing an inorganic oxide (such as Al2O3, AlO(OH), and SiO2), or titanium dioxide which has been subjected to a treatment employing an organic compound such as trimethylolethane, triethanolamine acetic acid salts, and trimethylcyclosilane, in addition to the above surface treatment.

Of these white particles, titanium oxide or zinc oxide is more preferably employed in view of prevention of coloring at a higher temperature or an increase of reflectance of elements arising from the reflective index.

In the present invention, aqueous polymers, which are substantially insoluble in electrolyte solvents, include a water-soluble polymer, and a polymer which has been dispersed in a water-based solvent.

Water-soluble compounds include proteins such as gelatin and gelatin derivatives; cellulose derivatives; natural compounds such as polysaccharides including starch, gum arabic, dextran, pullulan, or carrageenan; and synthetic polymer compounds such as polyvinyl alcohol, polyvinylpyrrolidone, acrylamide polymers, and derivatives thereof.

Gelatin derivatives include acetylated gelatin and phthalated gelatin. Polyvinyl alcohol derivatives include terminal alkyl group-modified polyvinyl alcohol and terminal mercapto group-modified polyvinyl alcohol. Cellulose derivatives include hydroxyethyl cellulose, hydroxypropyl cellulose, and carboxymethyl cellulose.

Further, compounds described in Research Disclosure and on pages 71-75 of JP-A 64-13546, and high water-absorptive polymers such as homopolymers of vinyl monomers having —COOM or —SO3M (M being a hydrogen atom or an alkaline metal) and copolymers of these vinyl monomers with each other and other vinyl monomers (for example, sodium methacrylate, ammonium methacrylate, and potassium acrylate) may be employed, which are described in U.S. Pat. No. 4,960,681 and JP-A 62-245260. These binders may be employed in combination of two or more of them.

In the present invention, gelatin and derivatives thereof, or polyvinyl alcohol and derivatives thereof may be preferably employed.

Polymers dispersed in water based solvents include latexes such as natural rubber latex, styrene butadiene rubber, butadiene rubber, nitrile rubber, chloroprene rubber, and isoprene rubber; and heat curable resins which are prepared by dispersing, in water based solvents, polyisocyanate based, epoxy based, acryl based, silicone based, polyurethane based, urea based, phenol based, formaldehyde based, epoxy-polyamide based, melamine based, or alkyd based resins, or vinyl based resins. Of these polymers, it is preferable to employ water based polyurethane resins described in JP-A No. 10-76621.

The phrase, "being substantially insoluble in electrolyte solvents", as described in the present invention, is defined as a state in which the dissolved amount per kg of the electrolyte solvents is at least 0 g and at most 10 g in the temperature range of −20 to 120° C. It is possible to determine the above dissolved amount employing the commonly known methods, such as a mass measuring method, or a component quantification method utilizing a liquid chromatogram or a gas chromatogram.

In the present invention, a preferred embodiment of the aqueous admixture of a water-based compound and titanium oxide is that the titanium oxide is dispersed in water according to the commonly known dispersion methods. The mixing ratio of a water based compound to titanium oxide is preferably in the range of 1 to 0.01 in terms of volume ratio, and is more preferably in the range of 0.3 to 0.05.

In the present invention, a medium, on which the aqueous admixture of a water-based compound and a white pigment is coated, may be located anywhere as long as it is located on the constitutional components between the counter electrodes of the display element. However, it is preferable that the medium is provided on the surface of at least one of the above counter electrodes. Examples of providing methods to the medium include a coating method; a liquid spraying method; a spraying method via a gas phase such as a method which jets liquid droplets employing vibration of a piezoelectric element such as a piezoelectric system ink-jet head, and a BUBBLE JET (registered trade name) ink-jet head which ejects liquid droplets employing a thermal head utilizing bumping; and a spray method in which liquid is sprayed via air or liquid pressure.

The coating method may be appropriately selected from any of the commonly known coating methods, and examples thereof include an air doctor coater, a blade coater, a rod coater, a knife coater, a squeeze coater, an impregnation coater, a reverse roller coater, a transfer roller coater, a curtain coater, a double roller coater, a slide hopper coater, a gravure coater, a kiss roller coater, a bead coater, a cast coater, a spray coater, a calender coater, and an extrusion coater.

Methods for drying the aqueous admixture of a water based compound and a white pigment provided on the medium are not particularly limited as long as they facilitate water evaporation. Examples thereof include heating employing a heating source, a heating method employing infrared radiation, and a heating method utilizing electromagnetic induction. Further, water evaporation may be performed under reduced pressure.

The term "porous", as described in the present invention, refers to the following state. The porous white scattering materials are formed by applying the above aqueous admixture of the water-based compound and the white pigment to the electrode and subsequently drying the resulting coating, after which, an electrolyte, containing silver or a compound containing silver in its chemical structure, is provided onto the aforesaid scattering material. Then, the resulting scattering material is sandwiched between counter electrodes. The above state is such that when electric potential is applied between the resulting counter electrodes, it is possible to cause silver dissolution and deposition reaction, and refers to a penetration state in which ion species are movable between the electrodes.

In the display element of the present invention, it is preferable that the water based compound in the above-described aqueous admixture is subjected to a hardening reaction employing a hardening agent during coating and drying thereof or after drying of the same.

Examples of hardening agents employed in the present invention include those described in the column 41 of U.S. Pat. Nos. 4,678,739, and 4,791,042, as well as JP-A Nos. 59-116655, 62-245261, 61-18942, 61-249054, 61-245153, and 4-218044.

Specific hardening agents include aldehyde based hardening agents (such as formaldehyde), aziridine based hardening agents, epoxy based hardening agents, vinylsulfone based hardening agents (such as N,N'-ethylene-bis(vinylsulfonylacetamido)ethane), N-methylol based hardening agents (such as dimethylolurea), boric acid, metaboric acid, and polymer hardening agents (compounds described in documents such as JP-A No. 62-234157). In case where gelatin is employed as a water-based compound, of the above hardening agents, it is preferable to employ vinylsulfone type hardening agents or chlorotriazine type hardening agents individually or in combination thereof. Further, in case where polyvinyl alcohol is employed, it is preferable to employ boron-containing compounds such as boric acid and metaboric acid.

The amount of these hardening agents employed is 0.001 to 1 g per gram of the water-based compound, and preferably is 0.005 to 0.5 g. In order to increase layer strength, a heat treatment or humidity regulation during the hardening reaction may also be carried out.

(Counter Electrode)

In the present invention, the counter electrodes include, for example, a carbon electrode, and a metal electrode, and a metal electrode is preferred. As a metal electrode, commonly known metals may be employed, such as platinum, gold, silver, copper, aluminum, zinc, nickel, titanium, bismuth, as well as alloys thereof. Preferred metals employed in the metal electrodes are those which exhibit a work function near the oxidation-reduction potential of silver in the electrolyte. Of these, a silver electrode or an electrode composed of silver in an amount of at least 80% is advantageous to maintain reduced silver, and further, excellent in preventing electrode contamination. As a method for preparing the electrode, conventional methods can be employed, such as a vacuum evaporation method, a printing method, an ink-jet method, a spin coating method, and a CVD method.

(Other Additives)

Constituting layers of the display element of the present invention may include subsidiary layers such as a protective layer, a filter layer, an antihalation layer, a cross-over light cutting layer, and a backing layer. If desired, may be incorporated in these subsidiary layers are various types of chemical sensitizers, noble metal sensitizers, sensitizing dyes, supersensitizing dyes, couplers, high-boiling solvents, antifoggants, stabilizers, development restrainers, bleach accelerators, fixing accelerators, color mixing inhibitors, formaldehyde scavengers, toning agents, hardening agents, surface active agents, thickening agents, plasticizers, lubricants, UV absorbers, anti-irradiation dyes, filter light absorbing dyes, fungicides, polymer latexes, heavy metals, antistatic agents, and matting agents.

These additives, described-above, are detailed in Research Disclosure, Volume 176 Item/17643 (December 1978); Volume 184 Item/18431 (August 1979); Volume 187 Item/18716 (November 1979); and Volume 308 Item/308119 (December 1989).

(Other Constituting Components of Display Element)

In the display element of the present invention, sealing agents, columnar structures, and spacer particles may, if desired, be employed.

Sealing agents are those which perform sealing so that leak to the exterior is minimized, and are called sealants. As the sealing agents, employable are heat curing, light curing, moisture curing, and anaerobic curing type resins such as epoxy resins, urethane based resins, acryl based resins, vinyl acetate based resins, en-thiol based resins, silicone based resins, or modified polymer resins.

Columnar structures provide a strong self-supporting capability (strength) between substrates, and include, for example, a cylindrical form, a quadrangular form, an elliptic from, and a trapezoidal form which are arranged at definite intervals in a specified pattern such as a lattice. Further, a stripe-shaped columnar structure, which is arranged at definite intervals, may also be employed. It is preferable that the columnar structures do not exhibit a random arrangement, but exhibit arrangements so that the distance between substrates is appropriately maintained and image display is not prevented, which arrangements include an equal distance arrangement, an arrangement in which intervals gradually varies, and an arrangement in which predetermined pattern is repeated at a definite cycle. When the columnar structures are such that the ratio of the area occupied by the display region of a display element is 1 to 40%, sufficient strength as a display element for commercial viability is obtained.

Between a pair of substrates, spacers for maintaining a uniform gap between the aforesaid substrates may be provided. As the above spacers, spheres composed of resins or inorganic oxides may be exemplified. Further, adhesion spacers, the surface of which is coated with thermoplastic resins, are suitably employed. In order to maintain a uniform gap between substrates, only columnar structures may be provided. However, both spacers and columnar structures may be provided, or, instead of the columnar structures, only spacers may be employed as space-maintaining members. The diameter of spacers, when a columnar structure is formed, is at most its height, and is preferably equal to the above height. When no columnar structure is formed, the diameter of the spacer corresponds to the thickness of the cell gap.

(Method for Driving Display Element)

Figure 5:
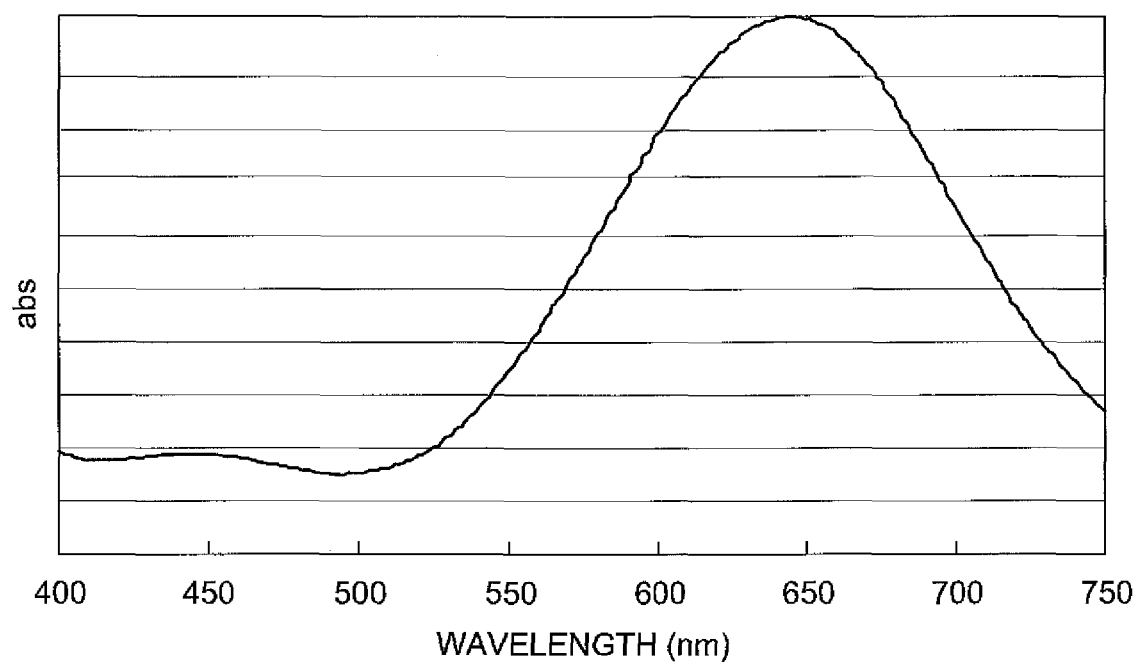
FIG. 5: Absorption spectrum of Example of Compound 1-46 in the oxidation state

Driving operation of the display element of the present invention may be simple matrix driving or active matrix driving. The simple matrix driving, as described in the present invention, refers to the driving method in which electric current is sequentially applied to a circuit in which a positive electrode line containing a plurality of positive electrodes faces a negative electrode line containing a plurality of negative electrodes so that each line intersects in the perpendicular direction. By employing the simple matrix driving, it is possible to simplify the circuit structure and the driving IC, resulting in an advantage of lower production cost. The active matrix driving refers to a method in which scanning lines, data lines, and current feeding lines are formed in a checkered pattern and driving is performed by TFT circuits arranged in each of the squares of the checkered pattern. Since it is possible to switch for each pixel, advantages result in gradation as well as memory function. For example, the circuit, described in FIG. 5 of JP-A 2004-29327, may be employed.

Hereinafter, examples of synthesis of electrochromic compounds of the present invention are described, and examples of other compounds may be synthesized according to the above examples.

Synthesis of Example of Compound 1-1

To 20 ml of acetic acid, were added 2.34 g of 4-hydroxy-3,5-di-t-butylbenzaldehyde, 2.96 g of 4,4'-bis(ethyl amino)benzyl, and 9.25 g of ammonium acetate. Then, the reaction was heated to reflux for about 5 hours, after which the reacted solution was added dropwise to an aqueous solution of a mixture of 10 ml of ammonia water and 200 ml of water. The precipitated crystals were filtered, and the crystals were recrystallized from ethyl acetate to prepare 3.74 g (73.2%) of 4-(4,5-bis(4-ethyl amino)phenyl-1H-imidazole-2-yl)-2,6-di-t-butylphenol.

To 30 ml of dichloromethane, was added 3.06 g of the prepared 4-(4,5-bis(4-ethyl amino)phenyl-1H-imidazole-2-yl)-2,6-di-t-butylphenol, after which 2.94 g of 3-(triethoxysilyl)propyl isocyanate was added dropwise to the reaction, and then the resulting solution was stirred at room temperature for about 4 hours. The reacted solution was condensed, and subjected to a column chromatography to prepare 3.48 g (57.7%) of Example of Compound 1-1. The structure of the product was identified by 1H-NMR and mass spectrum. The spectral values are: 1H-NMR (600 MHz, $CDCl_3$) δ0.55(t, 4H), 1.11 (t, 6H), 1.19 (t, 18H), 1.40-1.41 (m, 4H), 1.49 (S, 18H), 3.17 (t, 4H), 3.72 (q, 4H), 3.78 (q, 12H), 7.14-7.21 (m, 4H), 7.37-7.64 (m, 6H). Absorption spectrum of Example of Compound 1-1 in the oxidation state is given in FIG. 1.

Synthesis of Example of Compound 1-6

To 20 ml of acetic acid, were added 2.34 g of 4-hydroxy-3,5-di-t-butylbenzaldehyde, 3.00 g of 4,4'-dinitrobenzyl, 0.93 g of aniline, and 4.68 g of ammonium acetate. Then, the reaction was heated to reflux for about 5 hours, after which the reacted solution was added dropwise to an aqueous solution of a mixture of 10 ml of ammonia water and 200 ml of water. The precipitated crystals were filtered, and recrystallized from ethyl acetate to prepare 2.40 g (40.6%) of 4-(4,5-bis(4-nitrophenyl)-1-phenyl-1H-imidazole-2-yl)-2,6-di-t-butylphenol.

To 240 ml of ethyl acetate, was added 2.40 g of the prepared 4-(4,5-bis(4-nitrophenyl)-1-phenyl-1H-imidazole-2-yl)-2,6-di-t-butylphenol, and 0.12 g of 5% palladium/carbon catalyst. After that, air in the reaction vessel was replaced with hydrogen gas, and then the reaction was reacted at room temperature for about 4 hours. After the reaction was completed, the catalyst was filtered off, and the filtrate was condensed to prepare 2.15 g (100.0%) of 4-(4,5-bis(4-aminophenyl)-1-phenyl-1H-imidazole-2-yl)-2,6-di-t-butylphenol.

Figure 2:
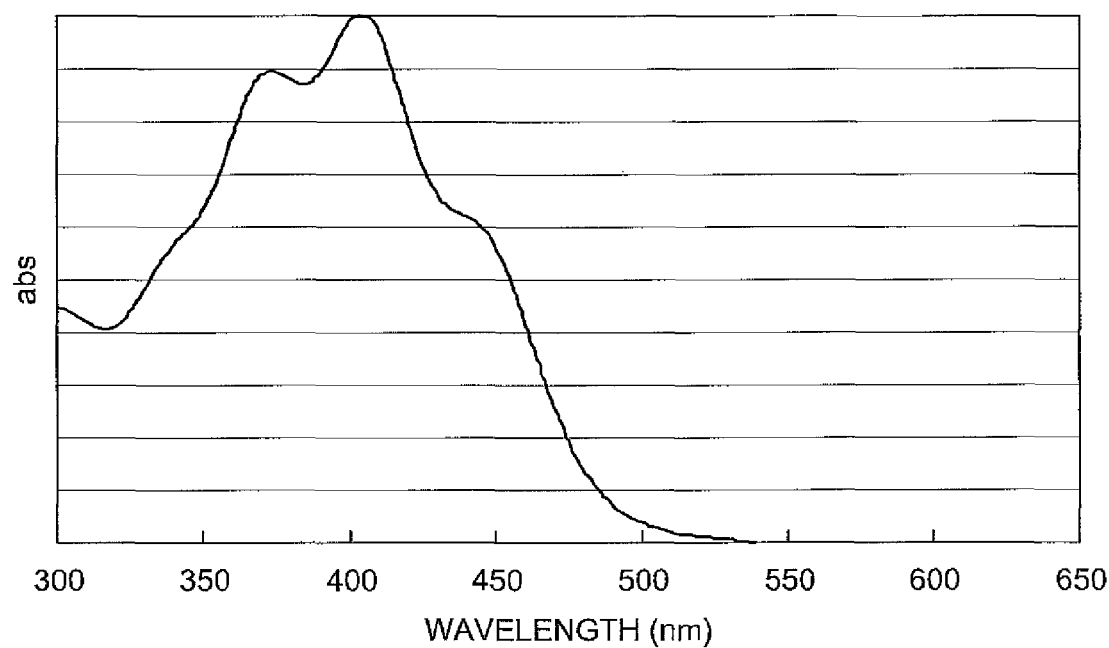
FIG. 2: Absorption spectrum of Example of Compound 1-6 in the oxidation state

To 20 ml of dichloromethane, was added 2.15 g of the prepared 4-(4,5-bis(4-aminophenyl)-1-phenyl-1H-imidazole-2-yl)-2,6-di-t-butylphenol, after which 2.01 g of 3-(triethoxysilyl)propyl isocyanate was added dropwise in the resulting solution, and then, the reaction was stirred at room temperature for about 4 hours. The reacted solution was condensed, and subjected to a column chromatography to prepare 2.86 g (68.6%) of Example of Compound 1-6. The structure of the product was identified by 1H-NMR and mass spectrum. The spectral values are: 1H-NMR (600 MHz, $CDCl_3$) δ0.55 (t, 4H), 1.40-1.41 (m, 4H), 1.49 (S, 18H), 3.17 (t, 4H), 3.55 (S, 18H), 7.14-7.21 (m, 4H), 7.37-7.64 (m, 11H). Absorption spectrum of Example of Compound 1-1 in the oxidation state is given in FIG. 2.

Synthesis of Example of Compound 1-24

To 30 ml of acetic acid, were added 0.83 g of 2,5-dihydroxy terephthalaldehyde, 2.10 g of benzyl, and 9.25 g of ammonium acetate. Then, the reaction was heated to reflux for about 5 hours, after which the resulted solution was added dropwise to an aqueous solution of a mixture of 10 ml of ammonia water and 200 ml of water. The precipitated crystals were filtered, and the crystals were subjected to suspension washing with ethyl acetate to prepare 1.63 g (59.6%) of 2,5-bis(4, 5-diphenyl-1H-imidazole-2-yl)benzene-1,4-diol.

Figure 3:
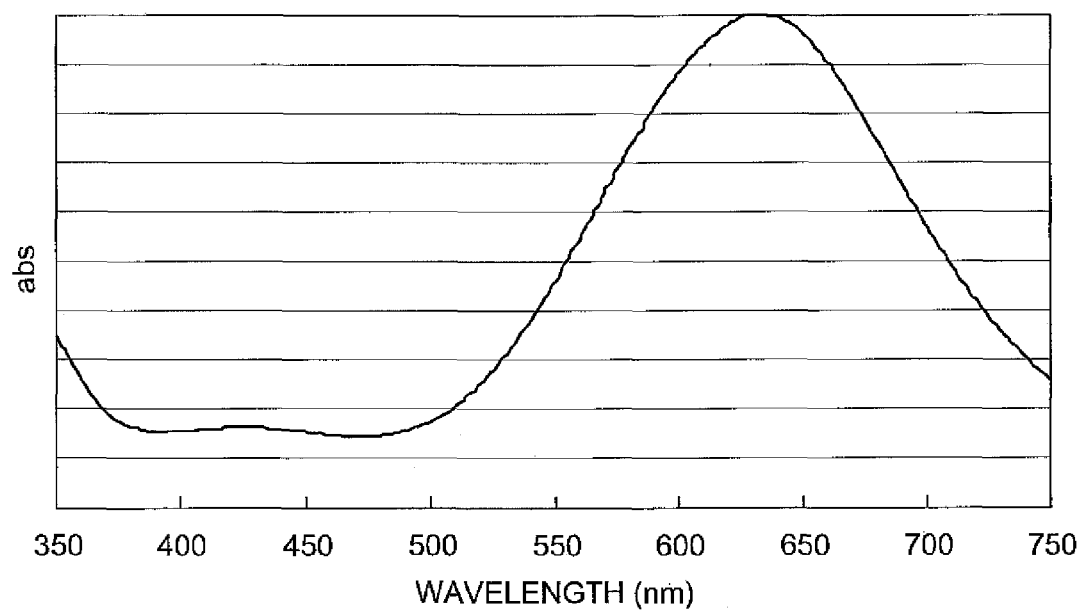
FIG. 3: Absorption spectrum of Example of Compound 1-24 in the oxidation state

To 30 ml of dichloromethane, was added 1.63 g of the prepared 2,5-bis(4,5-diphenyl-1H-imidazole-2-yl)benzene-1,4-diol, after which 1.48 g of 3-(triethoxysilyl)propyl isocyanate was added dropwise to the resulting solution, and then the reaction was stirred at room temperature for about 4 hours. The reacted solution was condensed, and the resulting products were recrystallized from ethyl acetate to prepare 1.65 g (53.1%) of Example of Compound 1-24. The structure of the product was identified by 1H-NMR and mass spectrum. The spectral values are: 1H-NMR (600 MHz, $CDCl_3$) δ0.55 (t, 4H), 1.19 (t, 18H) 1.40-1.41 (m, 4H), 3.17 (t, 4H), 3.78 (q, 12H) 7.14-7.21 (m, 4H), 7.37-7.64 (m, 6H), 7.69 (S, 2H). Absorption spectrum of Example of Compound 1-24 in the oxidation state is given in FIG. 3.

Synthesis of Example of Compound 1-27

To 20 ml of tetrahydrofuran, were added 3.13 g of 4-t-butyl aniline, and 2.42 g of triethylamine, and the solution was iced. In the iced solution, 2.73 g of ethyl chloroglyoxylic acid was added dropwise to the resulting solution over 10 minutes, after which the solution was heated to room temperature, and stirred for about one hour. After completion of the reaction, 50 ml of water was added to the reacted solution, and extraction was carried out three times with ethyl acetate. The organic phase was dried over anhydrous magnesium sulfate and solvent was evaporated under reduced pressure to obtain 4.97 g (99.7%) of ethyl-2-(4-t-butylphenylamino)-2-oxoacetate.

To 100 ml of toluene, were added at room temperature 2.38 g of 4-vinylanilin and 3.82 g of 28% sodium methoxide (in methanol solution), and then, 4.97 g of the prepared ethyl-2-(4-t-butylphenylamino)-2-oxoacetate was added to the resulting mixture, the solution was then heated to reflux for about 8 hours. After that, 100 ml of water was added to the resulting solution, and extraction was carried out three times with ethyl acetate. The organic phase was dried over anhydrous magnesium sulfate and solvent was evaporated under reduced pressure to obtain 3.86 g (60.0%) of $N^1$-(4-t-butylphenyl)-$N^2$-(4-biphenyl)oxalamine.

To 50 ml of toluene, were added 3.86 g of the prepared $N^1$-(4-t-butylphenyl)-$N^2$-(4-biphenyl) oxalamine and 4.98 g of phosphorus pentachloride, and the reaction was heated to reflux for about one hour. The resulted solution was condensed to about 30 ml under reduced pressure, after which the condensed solution was cooled to −20° C. The precipitated crystals were filtered, which were then recrystallized with n-heptane to obtain 2.79 g (65.0%) of $N^1$-(4-t-butylphenyl)-$N^2$-(4-biphenyl)oxal imidoyl dichloride.

To 20 ml of acetonitrile, were added 1.80 g of the prepared $N^1$-(4-t-butylphenyl)-$N^2$-(4-biphenyl)oxal imidoyl dichloride, 0.52 g of formamidine acetate, and 1.77 g of triethylamine, and the reaction was heated to reflux for about 4 hours. The resulted solution was cooled to room temperature, after which the produced triethylamine hydrochloride was removed by filtration. The filtrate was condensed, and recrystallized from N,N-dimethylformamide to obtain 0.85 g (25.7%) of 2,6-bis(4-t-butylanilino)-3,7-bis(4-vinylanilino)-1,4,5,8-tetraaza fulvalene.

To 10 ml of dichloroethane, were added 0.85 g of the prepared 2,6-bis(4-t-butylanilino)-3,7-bis(4-vinylanilino)-1,4,5,8-tetraaza fulvalene, and 0.1 mg of $H_2PtCl_6.6H_2O$, and the reaction was heated to about 80° C., and then, 0.46 g of triethoxy silane was added dropwise to the resulting mixture. After the completion of dropping, the solution was reacted at about 80° C. for about four days, after which 50 ml of water was added to the resulted solution, and extraction was carried out three times with ethylacetate. The organic phase was dried over anhydrous magnesium sulfate and solvent was evaporated under reduced pressure, after which the residue was recrystallized from toluene to obtain 0.64 g (50.3%) of Example of Compound 1-27.

Figure 4:
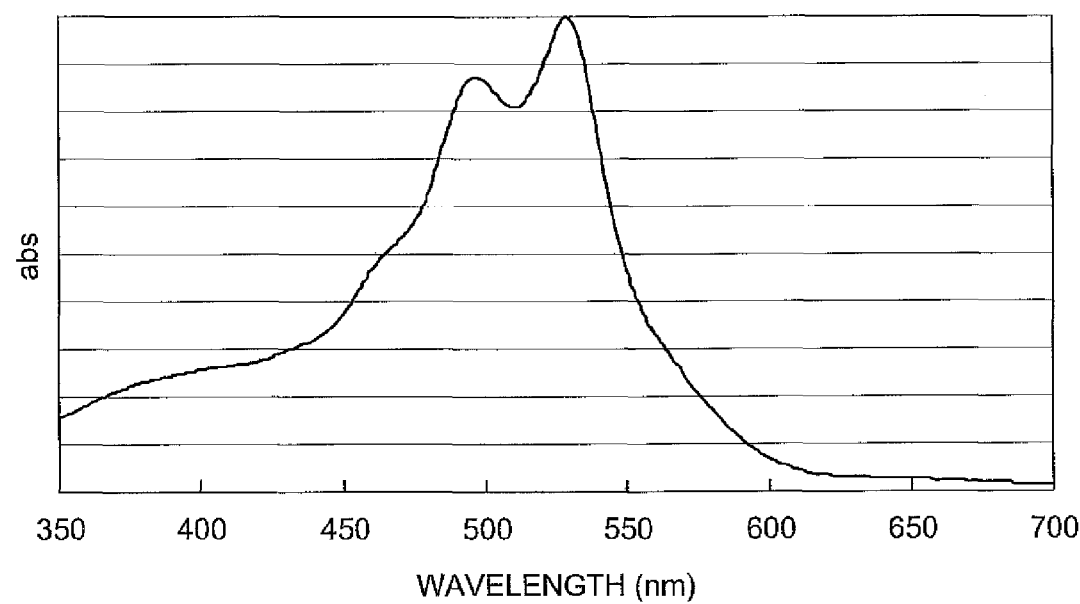
FIG. 4: Absorption spectrum of Example of Compound 1-27 in the oxidation state

The structure of the above product was identified by 1H-NMR and mass spectrum. The spectral values are: 1H-NMR (600 MHz, $CDCL_3$) δ0.91 (t, 4H), 1.19 (t, 18H), 1.35 (S, 18H), 3.78 (q, 12H), 3.83 (t, 4H), 7.01-7.40 (m, 16H). Absorption spectrum of Example of Compound 1-27 in the oxidation state is given in FIG. 4.

Synthesis of Example of Compound 1-46

To 50 ml of N,N-dimethyl sulfoxide, were added 6.15 g of 4,4'-bisfuluorobenzyl, 9.47 g of 1-allylpiperazine, and 10.35 g of potassium carbonate. Then, the reaction was heated to reflux for about 2 hours, after which, 100 ml of water was added into the resulted solution, and then, the extraction was carried out three times with ethyl acetate. The organic phase was dried over anhydrous magnesium sulfate and solvent was evaporated under reduced pressure, after which the residue was recrystallized from toluene to obtain 10.32 g (90.4%) of 4,4'-bis(4-allypiperazine)benzyl.

To 20 ml of acetic acid, were added 1.82 g of 4-hydroxy-3,5-dimethoxy benzaldehyde, 3.78 g of 4,4'-bis(4-allypiperazine)benzyl, and 9.25 g of ammonium acetate. Then, the reaction was heated to reflux for about 5 hours, after which the resulted solution was added dropwise to an aqueous solution of a mixture of 10 ml of ammonia water and 200 ml of water. The precipitated crystals were filtered, and the crystals were recrystallized from ethyl acetate to prepare 4.23 g (68.2%) of 4-(4,5-bis(4-(4-allypiperazine-1-yl)phenyl)-1H-imidazole-2-yl)-2,6-dimethoxyphenol.

To 50 ml of dichloroethane, were added 4.23 g of 4-(4,5-bis(4-(4-allypiperazine-1-yl)phenyl)-1H-imidazole-2-yl)-2,6-dimethoxyphenol, and 15 mg of $H_2PtCl_6.6H_2O$, and the reaction was heated to about 80° C., and then, 1.42 g of dimethyl chlorosilane was added dropwise to the resulting mixture. After the completion of dropping, the solution was reacted at about 80° C. for about four days, after which 100 ml of water was added to the resulted solution, and extraction was carried out three times with ethylacetate. The organic phase was dried over anhydrous magnesium sulfate and solvent was evaporated under reduced pressure, after which the residue was recrystallized from toluene to obtain 2.63 g (47.7%) of Example of Compound 1-46.

The structure of the above product was identified by 1H-NMR and mass spectrum. The spectral values are: 1H-NMR (600 MHz, $CDCl_3$) δ0.42 (S, 12H), 1.02 (t, 4H), 1.4 (m, 4H), 2.46 (t, 4H), 3.44 (S, 16H), 3.83 (S, 6H), 6.75-7.61 (m, 10H). Absorption spectrum of Example of Compound 1-46 in the oxidation state is given in FIG. 5.

EXAMPLES

The present invention will now be described in detail referring to examples. However, the present invention is not limited thereto The "part" or "%", which is used in the examples, represents "part by mass" or "% by mass", if not otherwise specified.

<<Preparation of Electrode>>

(Preparation of Electrode 1) Display Electrode+Display Layer

An ITO (Indium Tin Oxide) film, exhibiting a pitch of 145 μm and an electrode width of 130 μm, was formed on a glass substrate of 1.5 mm in thickness and 2 cm×4 cm in sizes according to commonly known methods to obtain a transparent electrode. On the transparent electrode, a film of 5 μm in thickness composed of titanium dioxide (having been subjected to necking treatment to form grains composed of about 4 to 10 particles of 17 μm in average particle size) was formed to prepare Electrode 1.

(Preparation of Electrode 2)

Adsorbing Solution 1, described below, was applied with about 100 mg/cm² onto the titanium dioxide film of Electrode 1. The electrode was allowed to stand at room temperature for about one hour. After that, the electrode was washed with ethanol and then water, and subsequently heated at 100° C. for about one hour to prepare Electrode 2.

(Preparation of Electrodes 3 to 6)

Electrodes 3 to 6 were prepared in a similar manner to the preparation of Electrode 1 except that Adsorption Solution 1 was changed to Adsorption Solutions 2 to 5, respectively.

<<Preparation of Adsorption Solution>>

Preparation of Adsorption Solution 1

A solution, in which 0.005 g of Example of Compound 1-1 was dissolved into 0.15 g of methanol, was added dropwise to a mixture of 0.02 g of acetic acid, 1 g of distilled water, and 1 g of methanol while stirring. The reaction was heated at room temperature for about one hour to prepare Adsorption Solution 1.

Preparation of Adsorption Solutions 2 to 5

Adsorption solutions 2 to 5 were prepared in a similar manner to the preparation of Adsorption Solution 1 except that Example of Compound 1-1 was changed to Example of Compounds 1-6, 1-24, 1-27 and 1-46, respectively.

(Preparation of Adsorption Solution 6): Comparative Example

To 2 g of toluene, were added at room temperature 0.1 g of 3-bromopropyl triethoxysilane and 0.1 g of triethylamine to prepare Adsorption Solution 6.

(Preparation of Adsorption Solution 7): Comparative Example

To 2 g of toluene, were added at room temperature 0.1 g of 3-aminopropyl triethoxysilane and 0.1 g of triethylamine to prepare Adsorption Solution 7.

(Preparation of Electrode 7)

A solution, in which Comparative Compound A was dissolved into a mixture of acetonitrile and ethanol so that the content of Comparative Compound A became 3 m mol/l, was applied onto Electrode 1 at 120 dpi via an ink-jet apparatus equipped with a head of piezoelectric system to prepare Electrode 7. The term "dpi" refers to the number of dots per 2.54 cm.

Compound A of Comparative Example

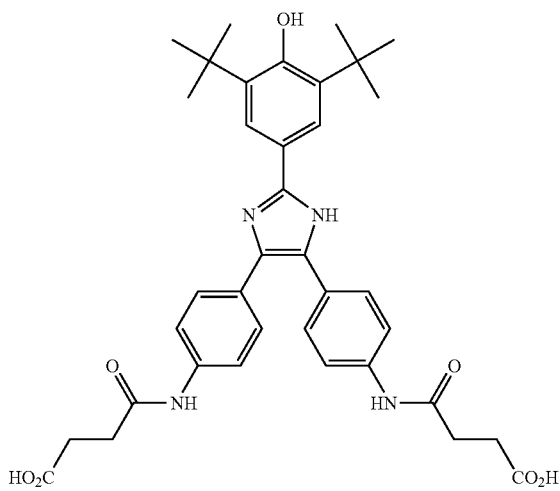

(Preparation of Electrode 8)

Electrode 1 was immersed in Adsorption Solution 6 and left for 24 hours, which was then washed with toluene. Further, the above electrode was immersed in a solution of 5% by mass of Compound B of Comparative Example at 80° C. for 100 hours, which was then washed with ethanol and then water to prepare Electrode 8.

Compound B of Comparative Example

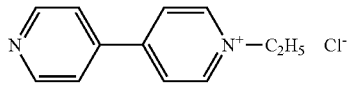

(Preparation of Electrode 9)

Electrode 1 was immersed in Adsorption Solution 7 and left for 24 hours, which was then washed with toluene. Further, the above electrode was immersed in a solution of N,N-dimethyl formamide containing 5% by mass of Compound A of Comparative Example and 3% by mass of 1-ethyl-3-(3-dimethyl aminopropyl)carbodiimide hydrochloride at room temperature for 100 hours, which was then washed with ethanol and then water to prepare Electrode 9.

(Preparation of Electrode 10): Counter Electrode

A nickel electrode, exhibiting an electrode thickness of 0.1 μm, a pitch of 145 μm, and a space of 130 μm between electrodes, was formed on a glass substrate of 1.5 mm in thickness and 2 cm×4 cm in sizes according to commonly known methods. The prepared electrode was further immersed in a substitution gold plating bath, to prepare a gold-nickel electrode (Electrode 10), a part of which was replaced with gold from the surface to the depth of 0.05 μm.

<<Preparation of Electrolyte>>

(Preparation of Electrolyte 1)

To 2.5 g of γ-butyrolactone, were dissolved 0.025 g of spiro-(1,1')-bipyrrolidinium tetrafluoroboric acid and 0.05 g of TEMPO (4-carboxy-2,2,6,6-tetramethylpiperidine 1-oxyl, free radical) to prepare Electrolyte 1.

<<Preparation of Display Element>>

(Preparation of Display Element 1): Electrode 2+Electrode 10+Electrolyte 1

The outer peripheral part of Electrode 10 was rimmed with an olefin based sealant containing spherical bead-shaped glass spacers of 40 μm in average particle size in an amount of 10% by volume fraction. Further, 20% by mass of titanium dioxide, CR-90, produced by Ishihara Sangyo Kaisha, Ltd., was added into an isopropanol solution containing 2% by mass of polyvinyl alcohol (exhibiting an degree of polymerization of 3,500 and a degree of saponification of 87%), after which the resulting solution was dispersed using an ultrasonic disperser to prepare an admixed solution. Then, on above Electrode 10, the above admixed solution was applied so that the dried film thickness became 20 μm. After that, resulting Electrode 10 was dried at 15° C. for 30 minutes to evaporate solvent, and then, dried at 45° C. for one hour.

Spherical bead-shaped glass spacers of 20 μm in average particle size were spread on the prepared titanium dioxide layer, after which, Electrode 10 and Electrode 2 were pasted together and pressed with heat to prepare an empty cell. Electrolyte 1 was charged into the aforesaid cell, and then, the inlet was sealed with an epoxy based ultraviolet curing resin to prepare Display Element 1.

(Preparation of Display Elements 2 to 8)

Display Elements 2 to 8 were prepared in a similar manner to the preparation of above Display Element 1 except that Electrode 2 was changed to Electrodes 3 to 9 respectively.

<<Evaluation of Display Element>>

[Evaluation of Reflectance Stability after Repeated Driving Cycles and Memory Characteristics]

Both electrodes of the prepared display element were connected to both terminals of a constant-voltage power supply. To Display Electrodes 1 to 6 and 8, voltage of −1.5 V was applied for 1.5 sec., and consequently, voltage of +1.5 V was applied for one sec. to display colored images, while to Display Element 7, voltage of +1.5 V was applied for 1.5 sec., and consequently, voltage of −1.5 V was applied for one sec. to display colored images. The reflectance of the above colored images was determined at the maximum absorption wavelength in a visible region via the spectrophotometric calorimeter CM-3700d, manufactured by Konica Minolta Sensing Inc.

The display element was driven ten times under the similar driving conditions. Then, thus obtained measured reflectance values were averaged, and the average value was denoted as $R_{ave3}$. Further, the display element was repeatedly driven 10 thousand times, after which $P_{ave4}$ was calculated in the similar manner to the above. $R_{color2}$ was defined as $R_{color2}=|R_{ave3}-R_{ave4}|$, which was used as an index of reflectance stability after repeated driving cycles.

The smaller the value of $R_{color2}$, the more excellent the reflectance stability after repeated driving cycles. Further, the voltage was turned off after colored images were displayed, and whether the colored state was maintained after ten minutes was visually evaluated.

TABLE 1

| | Electrochromic Compound | $\Delta R_{color2}$ (%) | Memory Characteristics | Remarks |
|---|---|---|---|---|
| Display Element 1 | Example of Compound 1-1 | 9 | A | Present Invention |
| Display Element 2 | Example of Compound 1-6 | 12 | A | Present Invention |
| Display Element 3 | Example of Compound 1-24 | 10 | A | Present Invention |
| Display Element 4 | Example of Compound 1-27 | 6 | A | Present Invention |
| Display Element 5 | Example of Compound 1-46 | 14 | A | Present Invention |
| Display Element 6 | Comparative Compound A | 26 | B | Comparative Example |

TABLE 1-continued

| | Electrochromic Compound | $\Delta R_{color2}$ (%) | Memory Characteristics | Remarks |
|---|---|---|---|---|
| Display Element 7 | Comparative Compound B | 22 | C | Comparative Example |
| Display Element 8 | Comparative Compound A | 19 | A | Comparative Example |

A: Colored state is maintained.
B: Images are colored, but the density decreases.
C: No colored state is maintained.

As is clearly shown in Table 1, it is found that, since the electrochromic compounds of the present invention exhibit excellent memory characteristics, as well as excellent fixed state of the electrochromic compound, the reflectance stability after repeated driving cycles is improved. Further, it is possible to very simply and easily produce the display element.

Description of Numeric Designations
1. Display Electrode
2. Display Layer
3. Electrolyte
4. White Scattering Layer
5. Counter Electrode

What is claimed is:

1. An electrochromic compound represented by Formula (1),

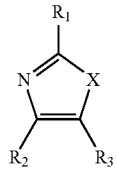

Formula (1)

wherein $R_1$ is a para-hydroxy phenyl group which may have a substituent in addition to the para-hydroxy group; $R_2$ and $R_3$ are each a hydrogen atom or a substituent; X is $N—R_4$, an oxygen atom, or a sulfur atom; and $R_4$ is a hydrogen atom or a substituent; provided that at least one of $R_1$-$R_4$ has a partial structure represented by Formula (2), $$—Si(Y)_n R'_{(3-n)}$$ Formula (2)

wherein Y is a halogen atom or OR, R is selected from the group consisting of a methyl group, an ethyl group, a propyl group, an isopropyl group, a t-butyl group, a pentyl group, a hexyl group, an octyl group, dodecyl group, a tridecyl group, a tetradecyl group, a pentadecyl group, a chloromethyl group, a trifluoromethyl group, a trichloromethyl group, a tribromomethyl group, a pentafluoroethyl group, a methoxyethyl group a phenyl group, and a naphthyl group, p-tolyl group, a m-chlorophenyl group, and a o-hexadecanoyl aminophenyl group; R' is an alkyl group, an alkenyl group, an aryl group, or a heterocyclic group, and n is an integer of 1-3.

* * * * *